US006615073B1

(12) United States Patent
Panescu et al.

(10) Patent No.: US 6,615,073 B1
(45) Date of Patent: *Sep. 2, 2003

(54) UNIFIED SWITCHING SYSTEM FOR ELECTROPHYSIOLOGICAL STIMULATION AND SIGNAL RECORDING AND ANALYSIS

(75) Inventors: Dorin Panescu, Sunnyvale, CA (US); William Reining, Cross Plains, WI (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/496,836

(22) Filed: Feb. 2, 2000

Related U.S. Application Data

(63) Continuation of application No. 09/100,653, filed on Jun. 19, 1998, now Pat. No. 6,101,410, which is a continuation-in-part of application No. 08/770,971, filed on Dec. 20, 1996, now abandoned.

(51) Int. Cl.⁷ ............................................. A61B 5/0428
(52) U.S. Cl. ....................................... 600/509; 600/522
(58) Field of Search ................................ 600/509, 522, 600/523, 300; 128/901; 607/9

(56) References Cited

U.S. PATENT DOCUMENTS

| | | | |
|---|---|---|---|
| 3,569,852 A | 3/1971 | Berkovits | 330/132 |
| 3,789,151 A | 1/1974 | Richards | 179/18 |
| 3,921,147 A | * 11/1975 | Fuhr et al. | 600/509 |
| 4,091,818 A | 5/1978 | Brownlee et al. | 128/419 |
| 4,631,686 A | 12/1986 | Ikawa et al. | 395/500.13 |
| 4,677,986 A | 7/1987 | DeCote, Jr. | 128/697 |
| 4,742,831 A | * 5/1988 | Silvian | 128/902 |
| 4,800,894 A | * 1/1989 | Milani | 128/901 |
| 5,040,209 A | 8/1991 | Greenberg et al. | 379/373 |
| 5,103,819 A | 4/1992 | Baker et al. | 128/419 |
| 5,172,481 A | 12/1992 | Wiseman et al. | 33/366 |
| 5,197,479 A | 3/1993 | Hubelbank et al. | 128/696 |
| 5,231,990 A | 8/1993 | Gauglitz | 128/697 |
| 5,247,751 A | 9/1993 | Ohya et al. | 33/561 |
| 5,339,262 A | 8/1994 | Rostoker et al. | 364/578 |
| 5,431,692 A | 7/1995 | Hansen et al. | 607/28 |
| 5,470,342 A | 11/1995 | Mann et al. | 607/5 |
| 5,494,042 A | 2/1996 | Panescu et al. | 128/695 |
| 5,503,160 A | 4/1996 | Pering et al. | 128/706 |
| 5,522,860 A | 6/1996 | Molin et al. | 607/20 |
| 5,570,059 A | 10/1996 | Vora et al. | 327/415 |
| 5,585,650 A | 12/1996 | Kumagai | 257/124 |
| 5,610,912 A | 3/1997 | Johnston | 370/359 |
| 5,722,402 A | * 3/1998 | Swanson et al. | 600/374 |
| 5,937,399 A | 8/1999 | Ohmi et al. | 706/33 |
| 6,221,012 B1 | * 4/2001 | Maschke et al. | 600/301 |

FOREIGN PATENT DOCUMENTS

| | | | |
|---|---|---|---|
| EP | 0613247 A2 | 8/1994 | H03K/19/00 |
| EP | 0613247 A3 | 8/1994 | H03K/19/00 |
| JP | 07299149 | 11/1995 | A61N/1/05 |
| WO | WO 93/06559 | 4/1993 | G06F/15/60 |

OTHER PUBLICATIONS

Kirsop, Doulgas, *Matrix Switches Remain A Test–System Mainstay*, Electronic Design, 37 Aug. 10, 1989, pp. 63–71.
Fletcher, An Engineering Approach to Digital Design, Prentice–Hall, 1980, pp. 212–216.*

* cited by examiner

*Primary Examiner*—Kennedy Schaetzle
(74) *Attorney, Agent, or Firm*—Bingham McCutchen LLP

(57) ABSTRACT

A cardiac mapping and pacing system includes a cardiac catheter having multiple electrodes and further includes an electrophysiological biological recorder. An interface system coupled between the multiple electrodes and the biological recorder permits the biological recorder to receive, process and display data acquired from the electrodes even though the number of electrodes may exceed the number of available inputs to the biological recorder. An application specific integrated circuit (ASIC) implemented as a CMOS switching circuit matrix is used to effectively interface a number of individual electrodes with a variety of existing and custom biological recorders.

21 Claims, 14 Drawing Sheets

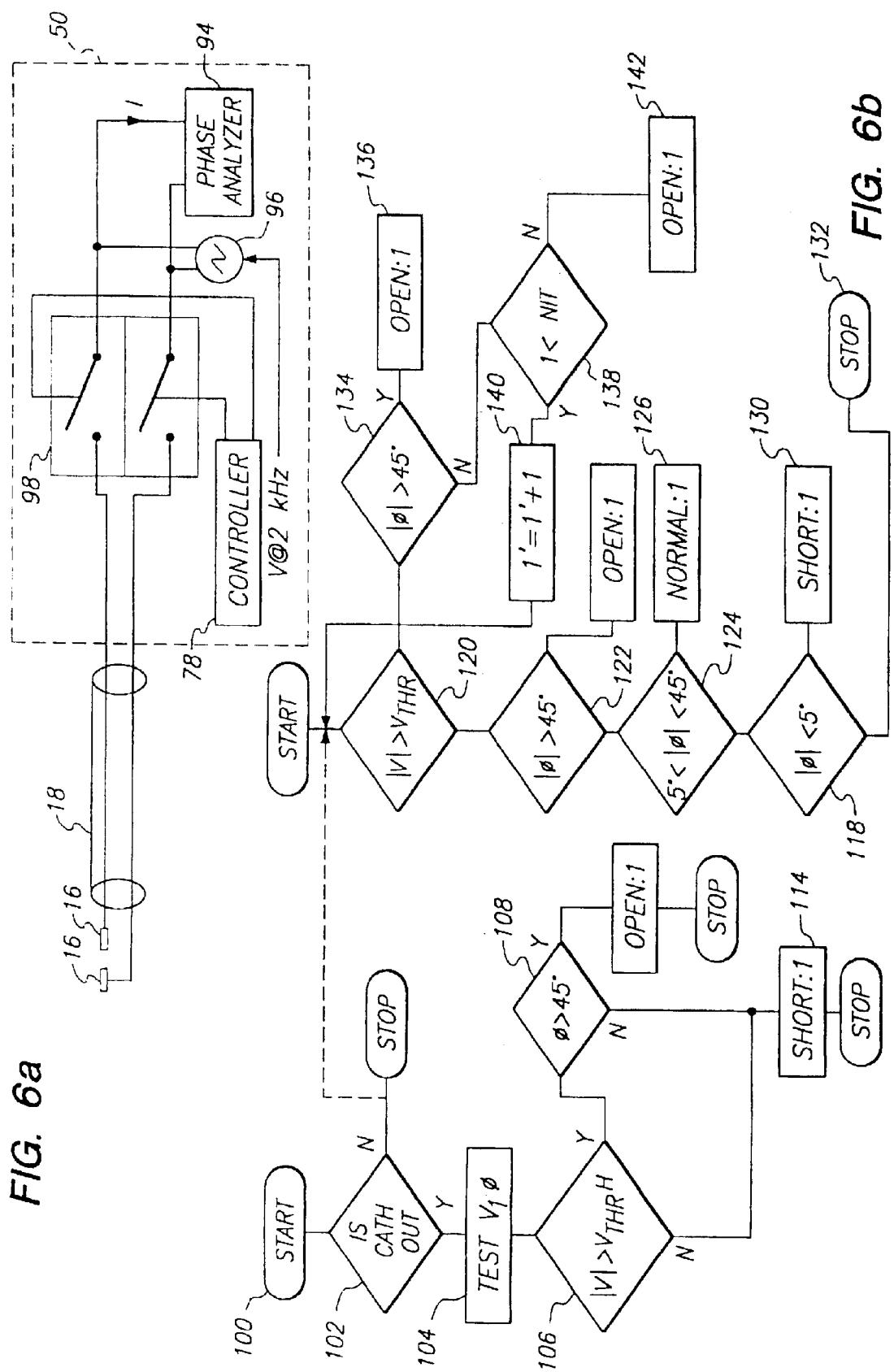

| BADDR R/W ∅∅ | ⊠ | B6 | B5 | B4 | B3 | B2 | B1 | B∅ |
|---|---|---|---|---|---|---|---|---|
| RADLE RW ∅1 | ⊠ | R6 | R5 | R4 | R3 | R2 | R1 | R∅ |
| COUNTER R/W 10 | C7 | C6 | C5 | C4 | C3 | C2 | C1 | C∅ |
| STATUS R 11 | 7 | 6 | 5 | 4 | 3 | = | 1 | ∅ |
| | TEST | CNT CHG | CNT UP/DN | CNT FNA | CNT DONE | INPUT OPEN | INPUT SHORT | SW ON |
| COMMAND W 11 | 7 | 6 | 5 | 4 | 3 | = | 1 | ∅ |
| | TEST SHORT | QUICK TEST | CNT UP/DN | CNT FNA | ⊠ | ⊠ | ⊠ | SW ON |

- ONLY ONE BIT SET TO 1 AT A TIME
- ALL OTHER OP-CODES ARE ILLEGAL
- NO ACTION WHEN ILLEGAL CODES DETECTED
- NON PHYSICAL SWITCHES SW$_{ON}$=0

FIG. 11

| COMMAND | D0 | D1 | D2 | D3 | D4 | D5 | D6 | D7 |
|---|---|---|---|---|---|---|---|---|
| RESET ALL TO USER DEFINED DEFAULTS | 1 | 0 | 0 | 0 | 0 | 0 | 0 | 0 |
| EXHAUSTIVE C/S TEST | 0 | 1 | 0 | 0 | 0 | 0 | 0 | 0 |
| BY: INPUT C/S TEST | 0 | 0 | 1 | 0 | 0 | 0 | 0 | 0 |
| ENABLE COUNT UP | 0 | 0 | 0 | 1 | 0 | 0 | 0 | 0 |
| ENABLE COUNT DOWN | 0 | 0 | 0 | 0 | 1 | 0 | 0 | 0 |
| DISABLE COUNT | 0 | 0 | 0 | 0 | 0 | 1 | 0 | 0 |
| SET SWITCH ON | 0 | 0 | 0 | 0 | 0 | 0 | 1 | 0 |
| SET SWITCH OFF | 0 | 0 | 0 | 0 | 0 | 0 | 0 | 1 |

*FIG. 12*

| $D_7$ | $D_6$ | $D_5$ | $D_4$ | $D_{3-0}$ |
|---|---|---|---|---|
| 0 | 0 | 0 | 0 | 0 |
| 1 | 0 | 0 | 0 | 1 |
| 0 | 0 | 0 | 0 | 2 |
| 1 | 0 | 0 | 0 | 3 |
| 0 | 0 | 0 | 0 | 4 |
| 1 | 0 | 0 | 0 | 5 |
| 0 | 0 | 0 | 0 | 6 |
| 1 | 0 | 0 | 0 | 7 |

*FIG. 13*

STATUS WORD

| D0 | D1 | D2 | D3 | D4 | D5 | D6 | D7 |
|---|---|---|---|---|---|---|---|
| SWITCH ON/OFF | SHORT | OPEN | COUNT COMPLETED | COUNT ENABLED | COUNT UP/DOWN | COUNT CHANGE | TEST |

*FIG. 14*

UNIFIED SWITCHING SYSTEM FOR ELECTROPHYSIOLOGICAL STIMULATION AND SIGNAL RECORDING AND ANALYSIS

RELATED APPLICATION DATA

This application is a continuation of U.S. patent application Ser. No. 09/100,653, filed Jun. 19, 1998, now U.S. Pat. No. 6,101,410 which is a continuation-in-part of U.S. patent application Ser. No. 08/770,971 filed on Dec. 20, 1996, now abandoned. Each of the above-identified applications are expressly incorporated herein by reference in their entirety.

BACKGROUND

This invention relates generally to cardiac pacing and mapping systems used in diagnosing and treating cardiac conditions. The invention also relates to electronic switching systems for programmably intercoupling multiple inputs with multiple outputs in pre-selected configurations. More particularly, the invention relates to an application specific integrated circuit (ASIC) operable to configure multiple input electrodes for cardiac signal recording and analysis or stimulation based on the immediate necessities of a particular electrophysiological procedure.

Advances in the cardiac mapping and pacing art have made it possible to acquire cardiac data through multiple channels. Known cardiac mapping and pacing catheters contain as many as sixty-four individual electrodes, each of which can be used for both mapping and pacing. Along with the flexibility, resolution and utility provided by such catheters comes the need to process the resulting data in an efficient, organized manner.

Various data acquisition systems have been developed for processing data acquired during cardiac mapping and pacing procedures. Typically, such systems record data through multiple recording inputs and process the data to assist the physician in making a diagnosis and rendering treatment. Some systems also include circuitry for generating pacing pulses that can be applied to the heart. Although effective in their intended application, known data acquisition systems become limited in their capabilities as advances in cardiac catheters provide ever increasing amounts of data. Many known data acquisition systems only support input from up to twenty-four electrodes and are not directly useful with catheters containing more than twenty-four electrodes. Because data acquisition systems are larger, more complicated and more expensive than the cardiac catheters used in mapping and pacing, it is impractical to redesign a data acquisition system each time an advance in the catheter art enables the acquisition of still more data. Nor is it economically sound for health care providers to retire still serviceable existing systems in favor of the latest model each time a new catheter is introduced. As advances are made in the catheter art, a need develops for adapting the new catheter to use with existing data acquisition systems.

The advances that can increase the demands on a data acquisition system are many and varied. For example, "impedance mapping" techniques have been developed wherein the resistivity of cardiac tissue is measured using an injected current. Infarcted cardiac tissue is detected by virtue of the lower electrical resistivity such tissue displays relative to healthy or normal tissue. Known data acquisition systems do not provide for the flexible electrode configuring and sequencing required or desirable in impedance mapping procedures. Similarly, existing data acquisition systems do not provide for automated sequencing and configuration of pacing electrodes. Nor do such systems provide for automatic detection of open or shorted electrodes. As the number of electrodes used in a procedure increases, so does the possibility of such malfunctions. Existing systems do not automatically and continuously monitor the electrodes to warn the physician in the event some of the electrodes are open or shorted. Absent an appropriate warning that some electrodes are no longer suitable for therapy or diagnosis, the delivery of effective therapy can be unknowingly prevented.

Known data acquisition systems for recording electrophysiological (EP) information have previously achieved switching capability through use of analog switch chips or mechanical switches in the system's signal conditioning circuitry. The ability to increase the number of potential electrode inputs was dependent on the particular system. Prior data acquisition systems were not designed for use with catheters containing large numbers of electrodes and did not provide the flexibility for configuring electrode subsets. Such prior systems also lacked open/short detection and automated pacing/switching capabilities.

SUMMARY OF THE INVENTION

The invention provides an application specific integrated circuit (ASIC) having a plurality of inputs, a plurality of outputs, a cross point switch matrix coupled to the inputs and to the outputs, and a control circuit coupled to the cross point switch matrix for controlling the cross point switch matrix to couple selected ones of the inputs with selected ones of the outputs in accordance with applied commands.

The invention also provides an ASIC operable to couple biological signals sensed by a plurality of biological electrodes with a plurality of input channels of an biological recorder. The ASIC includes a plurality of inputs operable to receive the biological signals sensed by the biological electrodes and a plurality of outputs that can be coupled to individual ones of the input channels of the biological recorder. The ASIC further includes a cross point switch matrix coupled to the inputs and the outputs. The ASIC further includes a control circuit coupled to the cross point switch matrix for controlling the cross point switch matrix to couple selected ones of the inputs with selected ones of the outputs in accordance with applied commands and thereby direct the biological signals sensed by selected ones of the biological electrodes with selected ones of the biological recorder input channels.

The invention also provides an ASIC operable to couple biological signals sensed by a plurality of biological electrodes with a plurality of input channels of an biological recorder. The ASIC includes a plurality of input operable to receive the biological signals sensed by the biological electrodes, a plurality of outputs that can be coupled to individual ones of the input channels of the biological recorder, a cross point switch matrix coupled to the inputs and to the outputs, an edge detector coupled to the cross point switch matrix and operable to detect the edges of applied electrical pulses, an edge counter coupled to the edge detector, test circuitry coupled to the cross point switch matrix operable to detect shorted and open conditions in the biological electrodes, and a control circuit coupled to the cross point switch matrix, the edge detector, the edge counter and the test circuitry for controlling the cross point switch matrix to couple selected ones of the inputs with selected ones of the outputs in accordance with applied commands and thereby direct the biological signal sensed by selected ones of the biological electrodes with selected ones of the biological recorder input channels.

It is an object of the invention to provide a new and improved interface system for coupling a number of cardiac electrodes to an biological recorder having the same number or fewer input channels than the number of electrodes.

It is a further object of the invention to provide an interface system that provides complete flexibility in the possible connections between the available inputs and available outputs.

It is a further object of the invention to provide an interface system that permits bi-directional transfer of signals between the available inputs and the available outputs.

It is a further object of the invention to provide an interface system that provides for pacing through the electrodes using externally generated stimulator pulses.

It is a further object of the invention to provide an interface system that provides pace pulse detection, counting and sequencing for particular diagnostic procedures.

It is a further object of the invention to provide an interface system that provides appropriate in-out connectivity for impedance mapping based on four or two electrode methods.

It is a further object of the invention to provide an interface system that automatically detects abnormal operating conditions such as open or shorted electrodes.

It is a further object of the invention to provide an interface system that automatically identifies the electrodes and biological recorder channels and that automatically verifies proper lead connections.

It is a further object of the invention to provide an interface that can be operated via an external, microprocessor-based control system.

It is a further object of the invention to provide an interface that compensates for pacing overvoltages and resulting polarization overpotentials so as to avoid biological recorder saturation.

It is a further object of the invention to avoid the saturation of a biological recorder by providing an interface that decouples pacing inputs from recorder outputs based on comparison with a threshold.

It is a further object of the invention to avoid the saturation of a biological recorder by providing an interface that decouples pacing inputs from recorder outputs based on ascertaining the pacing rate and/or pulse duration.

It is a further object of the invention to avoid the saturation of a biological recorder by providing an interface that decouples pacing inputs from recorder outputs based on analysis of pacing pulse derivative.

It is a further object of the invention to avoid the saturation of a biological recorder by providing an interface that connects decoupled outputs to known voltages.

It is a further object of the invention to avoid the saturation of a biological recorder by providing an interface that uses adaptive filtering removal of paced-induced voltages.

It is a further object of the invention to provide an interface that can be implemented in the form of an application specific integrated circuit (ASIC).

BRIEF DESCRIPTION OF THE DRAWINGS

The features of the present invention which are believed to be novel are set forth with particularity in the appended claims. The invention, together with the further objects and advantages thereof, may best be understood by reference to the following description taken in conjunction with the accompanying drawings, wherein like reference numerals identify like elements, and wherein:

FIGS. 6(a) and 6(b) are, respectively, a simplified block diagram and a logic flow chart diagram useful in understanding the operation of the unified switching system in a short/open detection mode.

FIG. 11 is a chart showing the instruction sequence used in the unified switching system.

FIG. 12 is a table showing one preferred format for command words used to control the function and operation of the ASIC.

FIG. 13 is a table showing an alternative format wherein parity checking is provided.

FIG. 14 is a table showing one preferred format for a status word used to reflect the current operational status of the ASIC during ASIC operation.

DETAILED DESCRIPTION OF THE INVENTION

Figure 1:
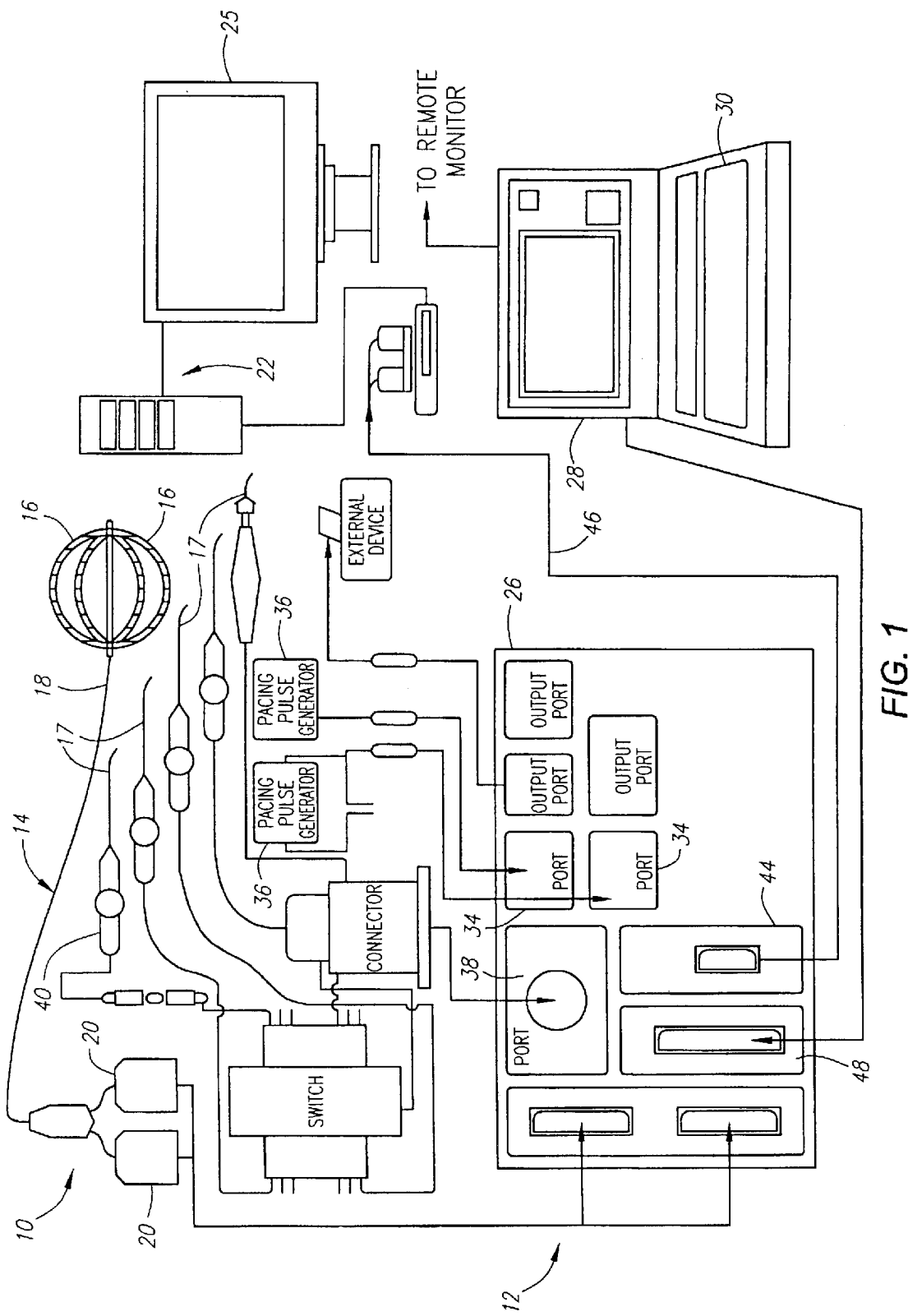
FIG. 1 is a simplified system diagram of a cardiac diagnostic system having a multiple electrode cardiac catheter, an biological recorder system and an interface unit having a unified switching system that couples the catheter with the biological recorder and that embodies various aspects of the invention.

Referring to the drawings, and in particular to FIG. 1, a cardiac diagnostic system 10 having an interfacing system 12 embodying various aspects of the invention is shown. The diagnostic system 10 includes a multiple electrode catheter 14 deployable within the heart of a patient. The catheter 14, which can comprise a catheter of the type shown in U.S. Pat. No. 5,647,870 entitled Multiple Electrode Support Structures, issued to Kordis et al. and and commonly owned by the assignee hereof, includes up to sixty-four individual electrodes 16. The disclosure of the Kordis patent is expressly incorporated herein by reference. Each of the electrodes 16 is connected to an individual conductor in a multiple conductor cable 18. The cable 18 terminates in one or more connectors 20 through which electrical connection can be made to the individual conductors and, hence, to the individual electrodes 16.

The diagnostic system 10 further includes a biological recorder system 22 of known construction that broadly functions to record, store, analyze and display signals acquired by the electrodes 16 of the catheter 14 and other or diagnostic catheters 40, each having electrodes 17. The biological recorder system 22 includes a recording/processing unit 24 that records and processes acquired signals and further includes a display unit 25 that displays the acquired signals to the attending health care personnel. Although the biological recorder system 22 is not critical and can be any one of several existing available types, it will be understood that the number of inputs available on the biological recorder 22 is less than or equal to the number of electrodes 16 provided on the catheter 14 plus the total number of electrodes carried by the catheters 40. Accordingly, it is not possible simply to "plug" the catheters 14 and 40 into the system 22 and still be able to provide all features described herein.

In accordance with one aspect of the invention, the interfacing system 12 enables information acquired by the multiple electrodes 16 and 17 to be loaded into the biological recorder 22. To this end, the interfacing system 12 functions broadly to couple individual electrodes or groups of electrodes 16 and 17 to the biological recorder 22. By so coupling the electrodes, it is possible to route all the acquired data into the biological recorder even though the number of available inputs into the recorder may be less than the total number of electrodes.

As further illustrated in FIG. 1, the interfacing system 12 includes an interface unit 26 that is coupled between the catheter 14 and biological recorder 22. The interface unit 26 is also coupled to an external, user-actuable, microprocessor-based computer control such as a laptop computer 28. The interface unit 26 operates under the command of the computer 28 to interconnect individual electrodes 16 with individual inputs to the biological recorder 22. The computer 28, in turn, responds to requests and instructions entered onto a keyboard 30 by the health care personnel and commands the interface unit 26 to switch among the electrodes 16 as required to achieve the desired function. Commands. To configure/test the unified switching system are issued by the computer 28 through the keyboard 30.

It will be appreciated that the computer 28 can be programmed with pre-determined protocols that correspond to higher level commands entered on the keyboard 30 and that, when implemented, achieve the desired function. In this manner, the health care personnel need not concern themselves with the specifics of which electrodes are connected to which inputs of the biological recorder. Instead, the personnel can simply enter the control function they desire to achieve and the computer 28 and interface unit 26 then switch among the electrodes and inputs as needed to achieve the desired function. Because of the flexibility in programming provided by the computer 28, a variety of catheters can be successfully interfaced with a variety of biological recorders.

As further illustrated in FIG. 1, the interface unit 26 is provided with a plurality of input and output ports for connection to external devices. A first port 32 is provided for connection to the cardiac catheter 14. This port 32 accepts the connectors 20 of the catheter 14. Two additional ports 34 are provided for connection to up to two external pacing pulse generators or stimulators 36. Pacing pulses generated by the external pacing pulse stimulators 36 can be selectively coupled to any of the available cardiac electrodes 16 and 17 to permit cardiac pacing through any of the electrodes 16 and 17. Still additional ports 38 permit connection to diagnostic catheters 40. Still another port 44 is provided for connection to the biological recorder 22. A suitable cable 46 is provided and is made up on a "custom" basis depending upon the particular type of biological recorder that is used. Finally, still another port 48 is provided for connection to the computer 28.

Figure 2:
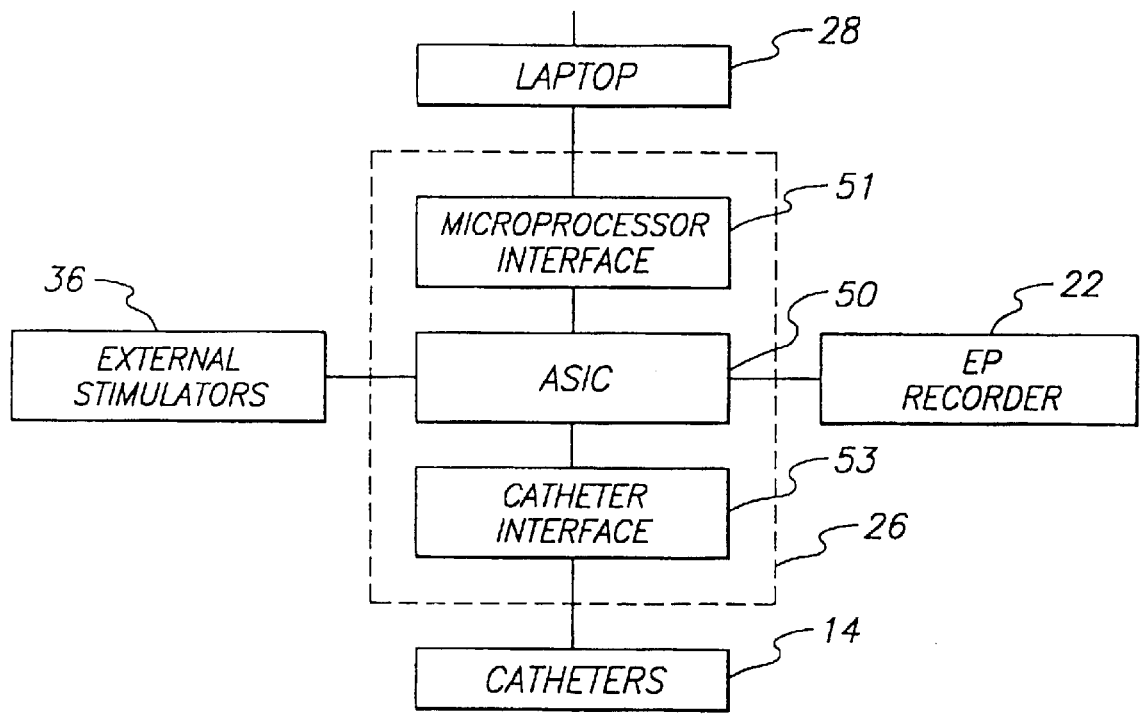
FIG. 2 is a simplified block diagram of the interface unit shown in FIG. 1 useful in understanding the operation thereof.

Referring to FIG. 2, the interface unit 26 is centered around an application specific integrated circuit (ASIC) 50 constructed in accordance with various features of the invention. The interface unit 26 includes a microprocessor-based interface 51 that serves as an interface between the external laptop computer 28 and the ASIC 50. The microprocessor interface 51, in response to high level instructions received from the laptop computer 28, generates appropriate control commands that are applied to the ASIC 50 to achieve the desired function. The various catheter electrodes 16, 17 are coupled to the ASIC 50 through appropriate catheter interface circuitry 53 that functions broadly to isolate the ASIC 50 from potentially damaging signals, currents and voltages that might be encountered by the various electrodes in the course of treating a patient. Such potentially damaging signals can include, for example, high voltage pulses externally applied to the patient's chest during the course of defibrillation. As illustrated, the ASIC 50 is also coupled to the external stimulators 36 and to the biological recorder 22.

Figure 3:
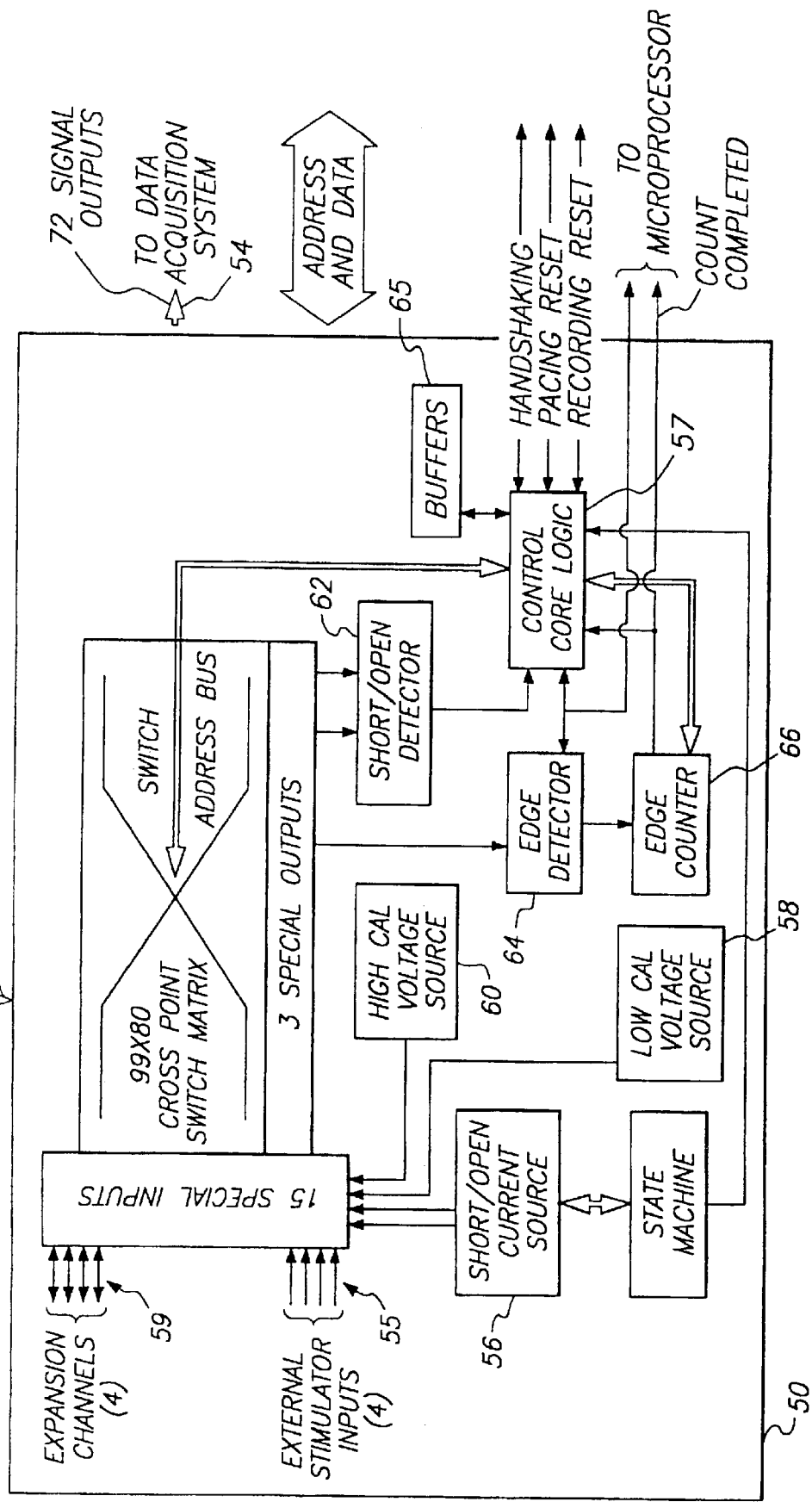
FIG. 3 is a block diagram of an application specific integrated circuit (ASIC) constructed in accordance with various aspects of the invention and useful in implementing the unified switching system shown in FIG. 1

Referring further to FIG. 2 and the ASIC system block diagram of FIG. 3, the ASIC 50, in the illustrated embodiment, includes ninety-six primary analog input pins 52 and seventy-two analog output pins 54. The ASIC 50 further includes four additional analog input pins 55 through which high level external signals, such as those produced by the external stimulators 36, can be received.

In general terms, the interface unit 26, and in particular the ASIC 50, are capable of providing various functions. For example, any of the input pins 52 can be connected to any of the output pins 54. This enables various subsets of the electrodes 16, 17 to be connected to various' subsets of the biological recorder inputs. In addition, any of the additional input pins 55 can be coupled to any of the primary input pins 52. This permits pacing pulses generated by any of the external stimulators 36 to be applied to the heart through any of the cardiac electrodes 16, 17. Finally, the ASIC 50 is capable of switching high level pacing pulse signals "backwardly" from any of the output pins to any of the input pins so as to permit "retrograde" pacing back through the interface unit 26. Pacing can thus be supported either from external pacing stimulators or from biological recorders that have pacing output capabilities.

Referring further to FIG. 3, the ASIC 50 comprises a cross point switch matrix that is controlled by an on-chip control and core logic circuit 57. The control/core logic circuit 57 responds to commands generated by the microprocessor interface 51 in response to higher level commands received from the computer 28 and configures the cross point switch matrix so as to establish desired electrical connections between the various electrodes, the external pacing stimulators 36 and the biological recorder 22. In addition, the ASIC 50 performs such other functions as detecting open or shorted electrodes, counting applied pacing pulses, electrode identification and confirmation of correct system connections.

As further illustrated in FIG. 3, four expansion channels 59 are provided for implementing an impedance mapping function of the type shown and described in connection with FIGS. 7(*a*) and 7(*b*) below. The expansion channels serve the purpose of applying and measuring signals needed for such impedance mapping. A constant current source 56 is provided for implementing an on chip test for open or shorted electrodes. A low voltage source 58 and a high voltage source 60 are also included. A pulse detection circuit or pulse detector 64 is provided for detecting the leading or trailing edges of pacing pulses applied through the ASIC 50, and an up/down edge counter 66 is provided for counting the number of pulses thus detected. In the preferred embodiment, the trailing edge is detected. Various buffer registers 65 are provided for system control and are coupled to the control/core logic.

As previously noted, signals can be transferred bidirectionally between the inputs and outputs, and pacing pulses can be applied "backwardly" through the ASIC 50 in "retrograde" fashion from any of the output pins 54 or external stimulator inputs 34 to any of the input pins 52. To avoid the possibility of switching among the various pins 52, 54 and 34 while a pacing pulse is being applied, the ASIC 50 preferably includes an edge detection and switch inhibition capability. To this end, the edge detector 64 senses the leading or rising edge of each pacing pulse and provides a signal each time the leading edge of a pulse is detected. The signal thus generated is used to inhibit switching of the cross point switch matrix while the pacing pulse is present. This ensures that the full width of the pacing pulse is delivered to the desired electrode and helps reduce the possibility of inducing ventricular fibrillation. Alternatively, switching may be forced to occur within a specified time after the trailing edge of the pacing pulse.

The pulse counter 66 responds to the pulse detection signals generated by the pulse detector 64 and increments or decrements the count in the counter 66 with each signal. In the illustrated embodiment, the counter is an eight bit counter and, hence, can support a count between zero and 255. The counter is under the control of the control/core logic 57 and, ultimately, the computer 28 and can be enabled or disabled by the computer 28 as desired or required. The ASIC 50 preferably supports reading/writing the count in the counter 66 without interruption of the count in progress. The ASIC 50 includes an output pin 68 for signaling the computer 28 when the count has been completed, i.e., has reached zero or 255.

In accordance with another aspect of the invention, the ASIC 50 provides for automatic detection of open or shorted electrodes. Given the large number of electrodes 16 that can be used in a mapping or pacing procedure, it is possible that one or more of the electrodes can be shorted or open. The short/open test function provided by the ASIC 50 helps alert the attending health care personnel to the existence of such malfunctions.

To provide for automatic short/open testing, the short/open current source 56 included in the ASIC 50 comprises a constant current source that can be selectively switched to each of the cardiac electrodes 16 under the command of the computer 28. In the event any of the electrodes is open, a high voltage condition will result when the constant current source 56 is coupled to that electrode. The short/open detector 62, which is also coupled to the electrodes along with the source 56, detects the occurrence of such a high voltage condition and interprets it as an open electrode. An appropriate signal is returned to the computer 28 which, in turn, generates an appropriate display for the attending personnel. The display preferably identifies which electrode is open. In the case of a shorted electrode, an abnormally low voltage results when the constant current source 56 is coupled to the electrode. Again, the short/open detector 62 detects the abnormal condition and signals the computer 28, which generates an appropriate display.

The high voltage source 60 and low voltage source 58 are also individually coupled to the outputs 54 under the control of the computer 28. The voltages thus applied to the outputs 54 can be used for identification of signals as well as for visual confirmation of correct connections by the operating personnel.

Figure 4:
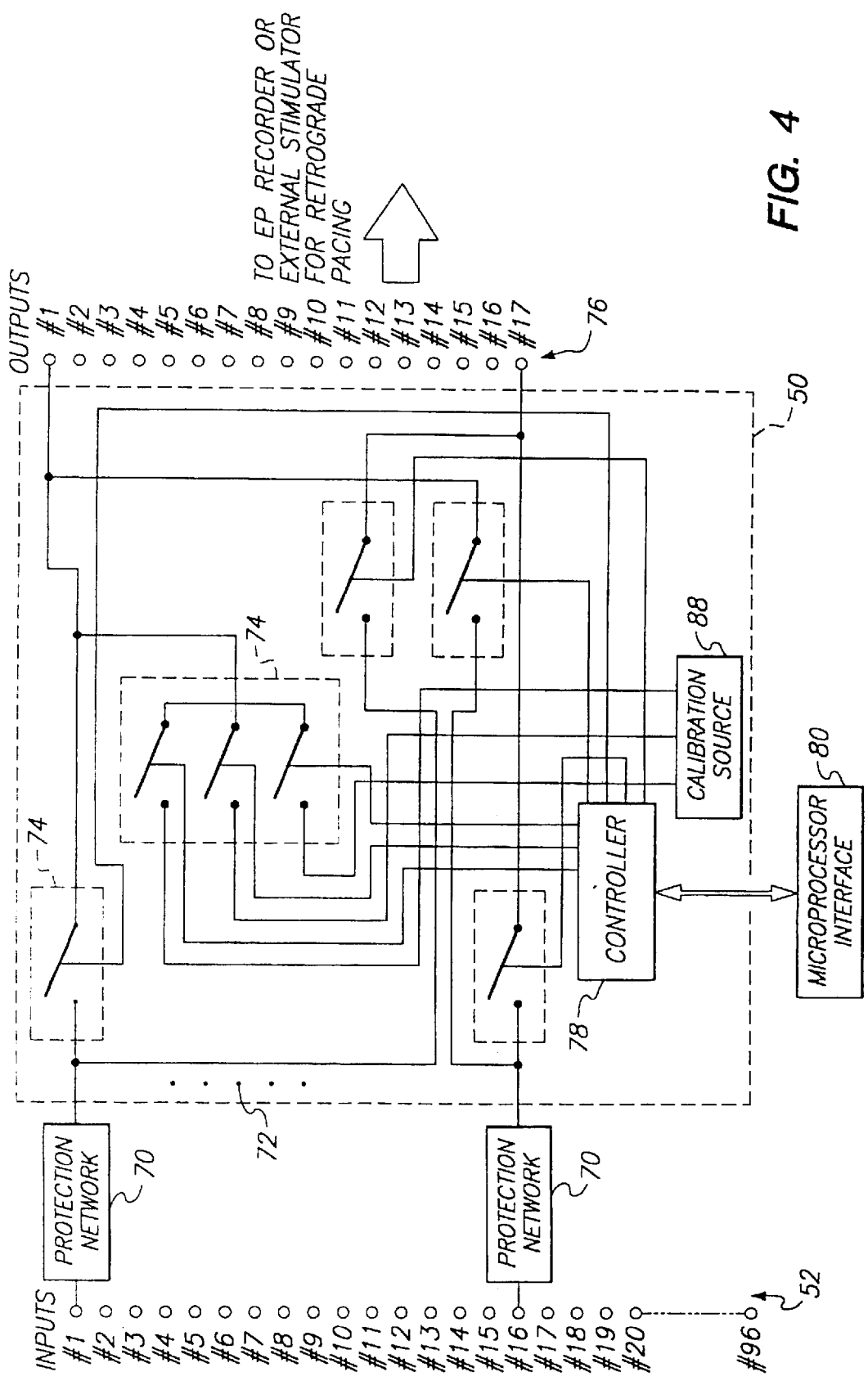
FIG. 4 is a functional block diagram of the ASIC shown in FIG. 3 useful in understanding the switching functions provided by the ASIC in a recording mode when the ASIC is used to interconnect a multitude of available electrodes with a sixteen channel biological recorder system.

Operation of the ASIC 50 in an electrode configuration mode can best be understood by reference to FIG. 4. As illustrated, each of the ninety-six individual inputs 52 is coupled through a protection network 70 to an input pin 72 of the ASIC 50. Within the ASIC 50, each input pin 72 is coupled through a separate, individually controllable switch 74 to each of a plurality of output pins 76 on the ASIC 50. Preferably, this function is implemented using a cross-point switch matrix (FIG. 3). Each of the switches 74 is under the control of a controller 78 that, in turn, is controlled by a microprocessor interface 80. The controller 78 actuates individual ones of the switches 74 so as to controllably connect any of the input pins 72 with any of the output pins 76. Accordingly, depending upon which of the switches 74 is actuated by the controller, any of the inputs 52 can be coupled to any of the outputs 76.

As further illustrated, each output pin 76 is also coupled through three independent, separately controllable switches 82, 84 and 86 to the zero, low and high voltage identification signal sources (collectively, reference numeral 88). Each of the switches is independently controlled by the controller 78. Accordingly, the controller can controllably and independently apply the zero volt, low voltage or high voltage identification signal to any of the output pins 76. It will thus be appreciated that the ASIC 50 in this manner provides complete flexibility in coupling any of the input pins 72 to any of the output pins 76 and in coupling any of the identification signal sources 88 to any of the output pins 76.

Figure 5:
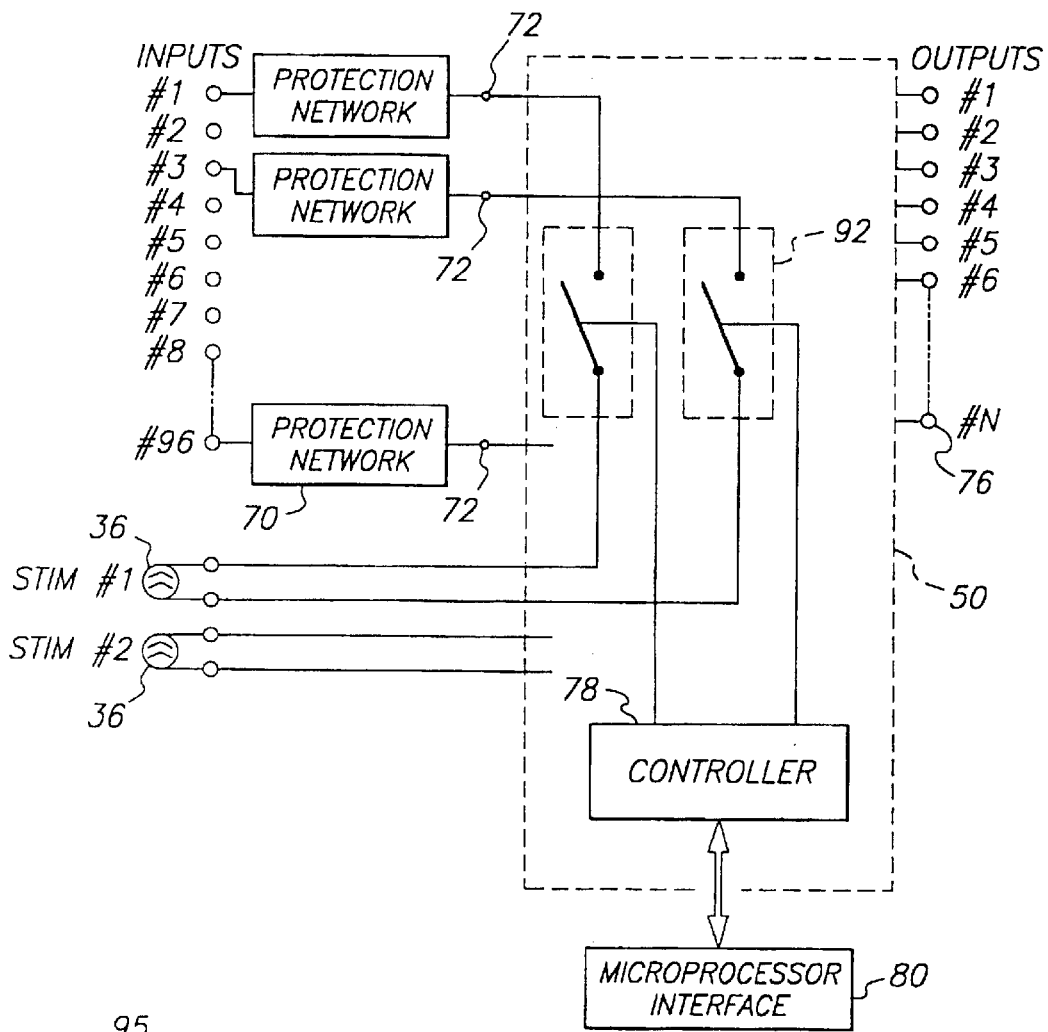
FIG. 5 is a simplified functional block diagram of the ASIC showing the ASIC in a pace switching, detection and counting mode.

Operation of the ASIC 50 in a pacing mode can best be understood by reference to FIG. 5. As illustrated, the external stimulators 36 are connected to the ASIC 50 through input pins 90. Each of the input pins 90 is coupled through a separate, individual, controllable switch 92 to each of the input pins 72. Each of the switches 92 can be separately actuated under the control of the controller 78 to couple the principal terminals of either stimulator 36 to any pair of input pins 72 and thus, to any pair of electrodes connected to those particular input pins 72. Again, the controller 78 responds to commands generated by the computer 28 and applied to the ASIC 50 through the microprocessor interface 80.

Operation of the ASIC 50 in a short/open detect mode can best be understood by reference to FIGS. 6(a) and 6(b). As illustrated in FIG. 6(a), a phase analyzer 96 is provided in addition to a constant frequency voltage source 94. Preferably, the voltage source 94 is a sine wave generator. Other waveforms, such as pulsed, rectangular or triangular, could be used. Preferably, the frequency of the signal generated by the source 94 is 2 kHz, and the current is less than 20 $\mu$A for safety. As illustrated, the voltage source 94 and phase analyzer 96 are connected to the electrodes through individually actuable switches 98 associated with each of the input pins 72 (FIG. 4). The switches 98, in turn, are under the control of the controller 78 that, by actuating selected ones of the switches 98, can couple the voltage source 94 and phase analyzer 96 to any of the electrodes 16. It will be appreciated that for purposes of this description, the controller 78 incorporates and integrates the functions of the control/core logic 57, the edge detector 64 and the edge counter 66. Similarly, it will be appreciated that the microprocessor interface 80 incorporates and integrates the functions of the high and low calibration voltage sources 60 and 58.

The operational logic used in sensing open and shorted electrodes is illustrated in the logic flow chart of FIG. 6(b). The system 12 is operable to test the status of the various electrodes both before and after the catheter 18 is placed in a patient's body. After the test sequence is initiated (box 100), the system verifies whether the catheter is in or out of the patient's body 102. If the catheter is outside the patient's body, the system then applies the alternating current to the electrodes in a preselected sequence and senses is the resulting voltages and phase relationships 104. If the magnitude of the resulting voltage exceeds a predetermined upper threshold $V_{thrh}$ 106, the system then checks whether the phase 0 is greater than a predetermined limit, which in the illustrated embodiment is 45° (108). If both criteria are met (i.e., $|V| \geq V_{thrH}$ and $\phi \geq 45°$), an open electrode condition is indicated (110). If the electrode voltage is less than a predetermined lower threshold $V_{thrL}$ 112, then a shorted electrode condition is indicated (114).

If it is determined at step 102 that the catheter is in place within the patient's body, the system then operates in a somewhat different mode. The alternating current is applied to the electrodes and the resulting voltage and phase are noted. If the resulting voltage is less than a predetermined threshold $V_{thr}$, 120 the system then checks to see whether the phase $\phi$ is less than a predetermined upper limit, which in the illustrated embodiment is again 45° (122). If the measured phase is less than the 45° limit, the system next checks to see whether the phase is between the 45° upper limit and a predetermined normal lower limit, which, in the illustrated embodiment, is 5° (124). If the measured voltage V is less than the threshold $V_{thr}$, and the measured phase $\phi$ is between the 45° and 5° upper and lower limits, then normal electrode operation is indicated (126). If the measured phase is less than the 5° lower limit 128, a shorted electrode condition is indicated (130) and further testing is stopped (132).

If the measured voltage V is determined to be above the threshold $V_{thr}$ at step 120, the system performs additional checks before concluding that the electrode is open. In particular, after determining that $|V| > V_{thr}$ at step 120, the system then compares the measured phase $\phi$ against the 45° upper limit (134). If $\phi > 45°$ then an open electrode condition is indicated (136). However, if $\phi < 45°$, system operation returns to step 120 where the measured voltage V is once again compared to the threshold $V_{thr}$. At the same time, a pointer i is initially set to "1" and is compared against a predetermined end point integer $N_{it}$ (138). If the current value of i is less than the end point integer $N_{it}$ system operation returns to step 120 where the measured voltage is once again compared to the threshold $V_{thr}$. If, this time, V is below the threshold, operation proceeds to step 122. If V remains above the threshold, the measured phase $\phi$ is once again compared against the 45° upper limit at step 134 while the pointer i is incremented by one. If this time the measured phase is above the 45° upper limit (134), an open electrode condition is indicated (136). If the measured phase 0 is below the 45° upper limit (134), system operation returns once again through step 138 to step 120. At the same time, the incremented pointer i is again compared against the end point integer $N_{it}$ (138). Operation in this "loop" mode continues until such time as (A) the measured phase $\phi$ exceeds the 45° upper limit (134) and an open electrode condition is indicated, (B) the measured voltage V remains above the threshold $V_{thr}$ for a number of cycles sufficient to increment the pointer i to the end point integer $N_{it}$ (140) and thereby confirm an open electrode condition (142) or (C) the measured voltage V drops below the threshold $V_{thr}$ as determined at step 120. Such operation helps guard against false indications of open electrodes.

Figure 7A:
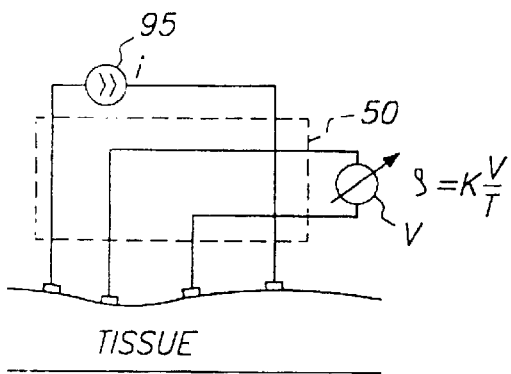
FIG. 7(a) is a simplified functional diagram illustrating on example of a four-electrode impedance mapping technique wherein the ASIC is used.
Figure 7B:
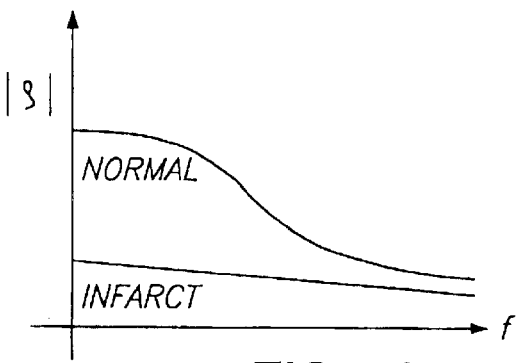
FIG. 7(b) is a graph showing measured impedance vs. frequency for both normal and infarcted cardiac tissue.

Operation of the ASIC 50 in an "impedance mapping" mode can best be understood by reference to FIGS. 7(a) and 7(b). In the impedance mapping mode, a variable frequency AC current is applied from a source 95 through the ASIC 50 and electrodes 16 to the tissue of the heart. The frequency of the applied current is changed and the applied current and resulting voltage across the cardiac tissue is measured. The resistivity ($\rho$) of the cardiac tissue is determined according to the relationship $\rho = K (V/I)$ where K is a constant, I is the applied current and V is the resulting voltage. As illustrated in FIG. 7(b), normal cardiac tissue is characterized in that the resistivity of the tissues drops with increasing frequency while infarcted tissue maintains a relatively constant resistivity largely independent of frequency. Accordingly, by applying an alternating current of changing frequency to the cardiac tissue and monitoring the resulting resistivity, areas of infarcted cardiac tissue can be located and differentiated from areas of normal cardiac tissue.

Figure 8A:
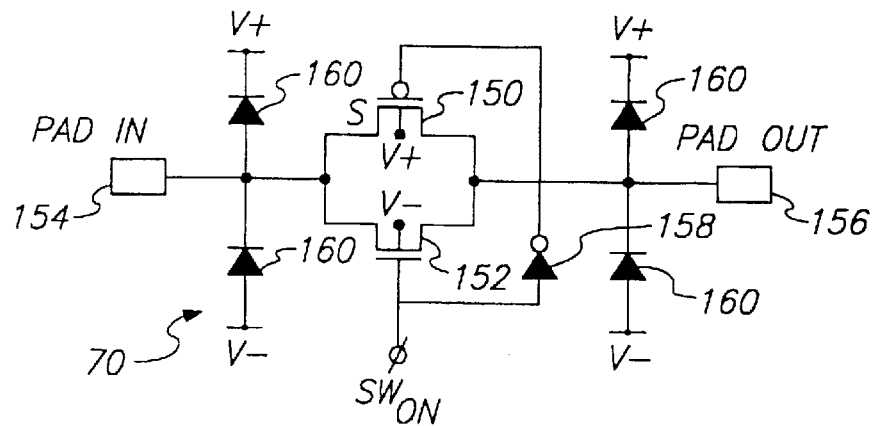
FIG. 8(a) is a simplified schematic diagram of a CMOS transmission gate used in implementing one embodiment of the ASIC.
Figure 8B:
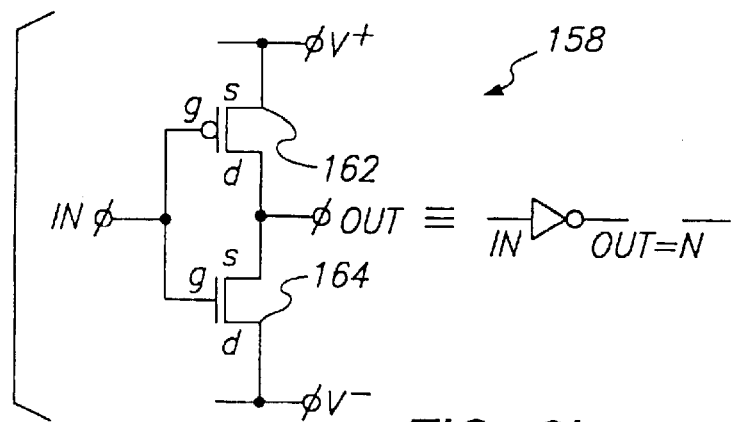
FIG. 8(b) is a simplified schematic diagram of an inverter used in conjunction with the transmission gate shown in FIG. 8(a).
Figure 8C:
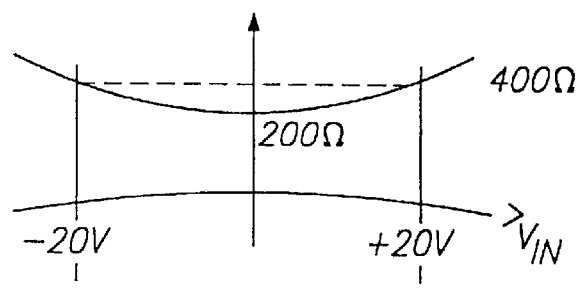
FIG. 8(c) is a graph showing the "on" resistance $R_{on}$ versus input voltage $V_{in}$ for the transmission gate shown in FIG. 8(a).
Figure 8D:
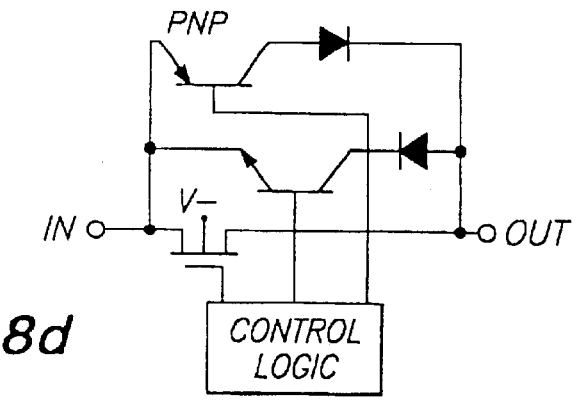
FIG. 8(d) is an alternate embodiment of a transmission gate useful in implementing one embodiment of the ASIC.
Figure 8E:
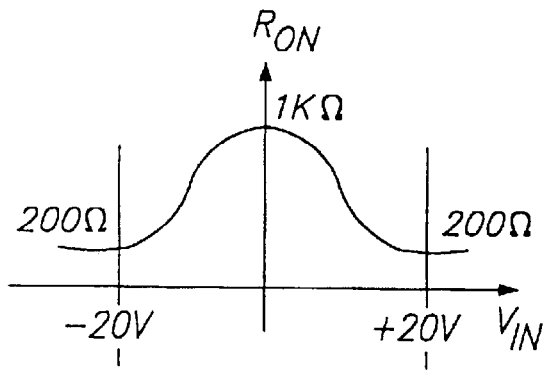
FIG. 8(e) is a graph showing the "on" resistance $R_{on}$ versus input voltage $V_{in}$ or the transmission gate shown in FIG. 8(d).

The operation of each of the switches 74 (FIG. 4) in the ASIC 50 can best be understood by reference to FIGS. 8(a) and 8(b). As illustrated, each switch 74 includes a PMOS transistor 150 having its principal electrodes connected in parallel with the principal electrodes of an NMOS transistor 152. The sources and drains of the transistors 150, 152, in turn, are connected between input and output pads 154, 156 associated with each switch 74. A control signal generated by the controller 78 is applied directly to the gate of the NMOS transistor 152 and through an inverter 158 to the gate of the PMOS transistor 150. An appropriately sensed control signal thus applied by the controller 78 enables the PMOS and NMOS transistors 150 and 152 jointly to pass signals in both directions between the pads 154 and 156. It should be noted that, depending upon the magnitude and polarity of the signals applied to the pads 154 and 156, either of the transistors 150 or 152 might be conductive at any instant when the controller 78 signals the switch 74 to turn "on".

As further illustrated in FIG. 8(*a*), static protection is provided in the form of reverse-biased diodes 160 connected between each of the pads 154 and 156 and the positive and negative polarity voltage sources V$^+$ and V$^-$.

The configuration of each inverter 158 is shown in FIG. 8(*b*). As illustrated, each inverter 158 includes a pair of MOS transistors 162 and 164 having, their principal electrodes connected in series between the positive and negative polarity voltage sources V$^+$ and V$^-$. The input to each inverter 160 is applied simultaneously to the gate of each transistor 162 and 164, and the output of each inverter is obtained between the transistors 162 and 164. A logic "high" voltage applied to the input biases transistor 164 "on" causing the negative polarity source voltage to appear at the output. Similarly, a logic "low" voltage applied to the input biases transistor 162 "on" thereby causing the positive polarity supply voltage to appear at the output. In this manner, the output voltage is opposite the input voltage thereby achieving the inversion function.

The transfer characteristics of the switch 74 shown in FIG. 8(*a*) is shown in FIG. 8(*c*). As shown, the "on" resistance R$_{on}$ of each switch 74 varies from a low of approximately 200Ω at an input voltage (V$_{in}$) of 0 volts to approximately 400Ω at V$_{in}$=+20V and V$_{in}$=−20V.

An alternate form of switch 741 is shown in FIG. 8(*b*). In this switch 741, the drain and source of an NMOS transistor 152' is shunted by an NPN transistor 151 and a PNP transistor 153. A forward biased diode 155, 157 is series connected with the collector of each transistor 151, 153. The bases of the transistors, as well as the control gate of the NMOS transistor, are coupled to the control logic 57. In this embodiment, maximum switch resistance is obtained when the applied input voltage V$_{in}$ is zero, and minimum switch resistance is obtained when the input voltage V$_{in}$ is at an extreme, i.e., at 20 V or −20V.

The switch transfer characteristics as shown in FIG. 8(*e*). As illustrated, the switch on resistance R$_{on}$ is approximately 1 KΩ at V$_{in}$=0 V, and is approximately 200Ω at V$_{in}$±20 V.

Figure 9:
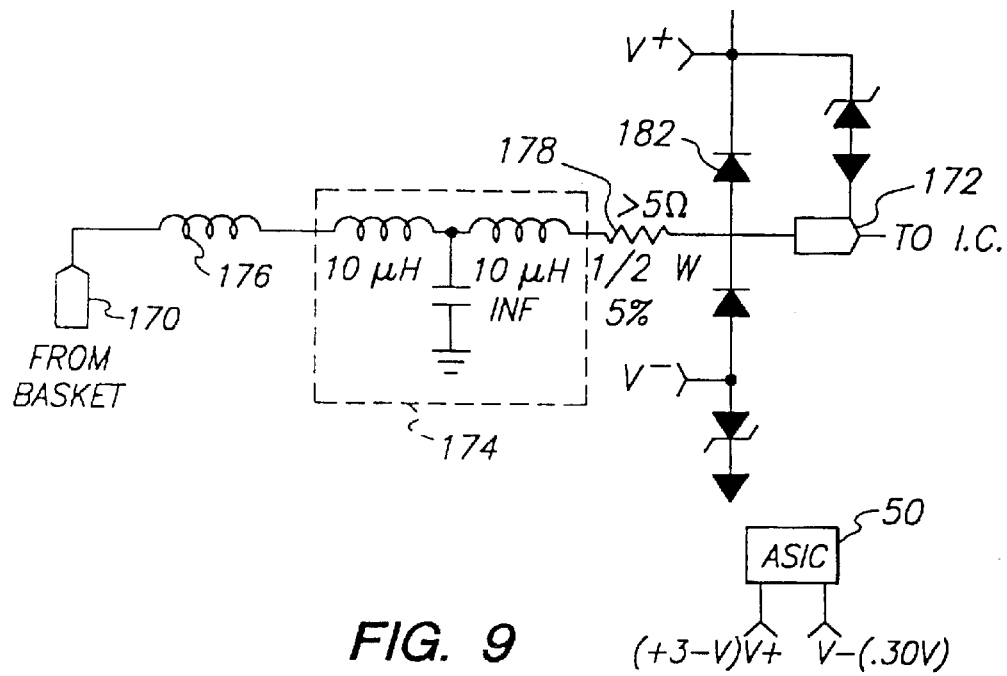
FIG. 9 is a schematic diagram of an external protection network usable in connection with the unified switching system.

The configuration of each protection network 71 is shown in FIG. 9. As illustrated, each protection network 71 includes an input node 170 and an output node 172. A "T" network low pass filter 174 is coupled through an inductor or "choke" 176 to the input node 170 and is coupled through a current limiting resistor 178 to the output node 172. A pair of diodes 180, 182 protect the ASIC inputs 172 from transient high voltages. The diodes 180, 182 connect to the ASIC power supply voltages V$^+$ and V$^-$. Overvoltage protection is provided by means of a pair of zener diodes 184, 186 that shunt to ground any voltages in excess of the zener voltage.

Figure 10:
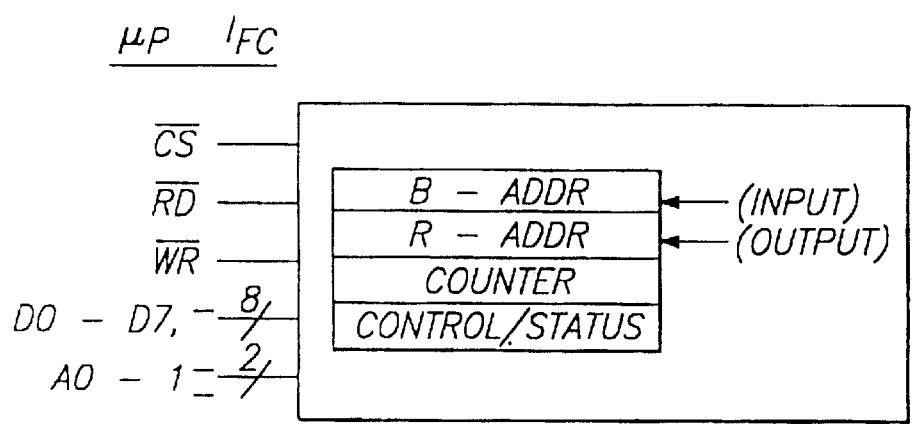
FIG. 10 is a diagrammatic illustration of the internal register structure of the unified switching system.

In the illustrated embodiment, the switching function provided by the ASIC 50 is controlled by writing control words to the chip. The control sequence consists of 8 bits of input address, 8 bits of output address and 8 bits of command data. These functions are implemented through an 8 bit microprocessor-compatible bus 70. Operation of the pulse counter 66 is similar. The control sequence contains 8 bits indicating the count loaded or to be read back with the remaining 8 bits of command data serving to enable or disable the counter and specify whether the counting function is to be up or down. As also illustrated, the ASIC 50 preferably provides a hardware "handshake" function that confirms that applied switching commands have been received and executed. In the illustrated embodiment, communication with the ASIC can best be understood by reference to FIGS. 10 and 11. As illustrated, the ASIC includes four registers for reading data into and out of the ASIC. The first register is a "B-ADDR" register that specifies the ASIC input to be connected. The second register is an "R-ADDR" register that stores the ASIC output to which the selected input connects. The third register is a "COUNTER" register that reflects the current count in the counter. The final register is a "CONTROL/STATUS" register that functions alternately to either receive an external "command" word for controlling ASIC operation or to receive an internally generated "status" word reflecting the current status of a particular system parameter.

As further illustrated, five different types of control inputs can be applied to the ASIC. The first is a "CHIP SELECT" (CS) command that operates to enable and disable the ASIC. The second and third control inputs are respective "READ" (RD) and "WRITE" (WR) commands that control whether data are to be read into or written out of the ASIC. The fourth control input is an eight bit data bus "D0–D7" through which eight bit data words can be written into or read out of the ASIC. The fifth control input is a two-bit input "A0–A1" used to select any one of four available, predetermined control functions provided by the ASIC.

During System operation, the microprocessor interface responds to instructions and commands entered by the system operator on the laptop computer and generates the appropriate chip commands to cause the ASIC to carry out the desired function.

In the illustrated embodiment, basic switching between the various input and output pins of the ASIC is achieved as follows. First, the ASIC is enabled by setting $\overline{CS}$=0. Next, the address of the desired input pin is written into the B-ADDR register. This is achieved by setting $\overline{RD}$=0 and $\overline{WR}$=1. The B-ADDR register is selected by applying a "00" control word to the control inputs A0–A1. The address of the selected input pin is applied to the data inputs D0–D7. The address thus specified is then written into the B-ADDR register.

The address of the desired output pin is written into the R-ADDR register in similar manner. To select the R-ADDR register, the control word "01" is applied to the control inputs A0–A1. The address of the desired output pin is applied to the data inputs D0–D7. In this case, the changed control word causes the data on the data inputs D0–D7 to be written into the R-ADDR register rather than the B-ADDR register. After thus receiving the specified addresses for a particular input pin and a particular output pin, the ASIC the enables the switches as needed to connect the specified input pin with the specified output pin. Various sets and subsets of input/output pin combinations can thus be specified and implemented by the ASIC by sequentially specifying the desired combinations to the ASIC in this manner.

Information is written into and out of the COUNTER register in similar manner. Such information can be written into the COUNTER register using the WRITE control input or can be read out of the register using the READ control command. Data transfer into or out of the COUNTER register is specified by applying the control word "10" to the control inputs A0–A1. The actual data to be written into or read out of the CONTROL register are communicated to and from the ASIC through the data inputs D0–D7.

Various additional control functions, such as testing for shorted or open electrodes, can be achieved by writing instructions into, and reading status information out of, the CONTROL/STATUS register. The CONTROL/STATUS register is accessed by applying the control word "11" to the control inputs A0–A1. Command words are written into the CONTROL/STATUS register through the data inputs D0–D7 by setting $\overline{RD}$=0. Status words are read out of the CONTROL/STATUS register by setting $\overline{WR}$=0.

The word (B-ADDR) is also used to select an identification voltage source. The word (RADDR) is also used to select a second input pin as needed for the open/short tests, a stimulator input, a short/open signal generator input or an expansion channel.

Pulse counter operation is controlled by applying the control word "10" to the control inputs A0–A1. An 8-bit command word can be written into the counter register ($\overline{RD}$=0), or the count in the register can be written out of the register ($\overline{WR}$=0) through the data inputs D0–D7. The available commands include count load/read back, enable/disable and up/down.

The detection of shorted and open electrodes can be performed either "exhaustively" or by specifying particular pairs. In the "exhaustive" test, all possible combinations of input and output pins are tested. Although effective in finding all potential malfunctions, such a test takes considerable time. Alternatively, the ASIC 50 can be operated so that tests for shorted conditions are performed only between specified pairs of inputs and outputs. Operating speed is considerably increased using such a test protocol. In the illustrated embodiment, selection between the "exhaustive" test and particular pair test is specified by setting selected bits of the status word to "1". For example, when D1=1 in the command word, the exhaustive test is performed. If D2=1 in the command word, then an open/short test is performed between two inputs defined by the B-ADDR and RADDR words.

The ASIC 50 preferably provides "command handshaking" to verify proper command receipt and execution. In the illustrated embodiment, appropriate control signals are generated in response to receipt of the various control commands and are reported back from the ASIC to the microprocessor interface to verify proper command receipt and execution.

One example of available command and status-word formats preferably employed in the ASIC 50 is shown in the table of FIG. 12. As illustrated, each bit of the 8-bit command word has a particular significance. When that bit is set to "1", the desired control function is achieved. Alternatively, and as illustrated in FIG. 13, binary combinations of up to 4 bits can be used to signify the desired control function, and the remaining 4 bits of the command word can be used as a parity check to ensure proper receipt of the desired command. In the embodiment illustrated in FIG. 13, for example, bits D0–D3 of the command word specify in binary form the desired command, and bits D4–D7 the parity number. By comparing the parity numbers of the two, four-bit sets, proper command receipt can be verified.

FIG. 14 shows in tabular form one available format for the status word. As illustrated, each bit of the 8-bit status word represents a particular status of various blocks of the ASIC. For example, D0=1 indicates that the switch selected for polling is ON. D1=1 indicates the presence of short circuits between selected inputs. D2=1 similarly indicates open conditions.

Preferably, the computer 28 includes software that stores and executes various "protocols" that have been developed in advance. The protocols, in turn, are designed to define and implement various desired pacing and recording switching configurations. As previously noted, the precise switching configurations actually implemented by the various protocols are determined by such factors as the nature, number and locations of the various electrodes employed by a particular catheter, the type and configuration of biological recorder or other data acquisition system employed and the particular diagnostic or therapeutic procedure being performed. Because the ASIC 50 permits complete bi-directional interconnectivity among the various input pins, output pins and on-chip sub-systems, considerable operating flexibility is provided and is limited primarily only by the capabilities of the computer 28 and the software therein contained.

In one embodiment, the ASIC 50 can be implemented using known 40–100 V BICMOS fabrication techniques. Preferably, a 2-micron feature size is employed. The IC package can be, for example, a QFP 240 (240 pin) or QFP 208 (208 pin) surface-mount plastic package. Alternatively, the ASIC 50 can be designed in a multi-die package. To ensure that electrograms are not distorted, the noise figure introduced by the ASIC 50 should be less than 30 GVRMS between 1 and 300 Hz. The impedance at frequencies below 2 kHz when any switch is "ON" is preferably less than 200Ω at higher input voltages. The impedance below 2 kHz when any switch is "OFF" is preferably greater than 500 kΩ. The insertion attenuation of pacing current directed to an individual catheter electrode is preferably better than –0.1 dB. The low identification voltage is preferably 1 mV while the high identification voltage is preferably 10 mV. It will be appreciated that, although these specified operating parameters and specifications are preferred for the application and in the embodiment herein described, other operating parameters and design specifications can be used. It will also be appreciated that other numbers of input pins, output pins, external source inputs etc., can be used beyond those shown and described.

The ASIC as shown and described herein is particularly well suited for certain applications. For example, it is sometimes desirable to apply pacing pulses to the heart and then record the resulting cardiac signals using the same set of electrodes. However, because the pacing pulse amplitude greatly exceeds the amplitude of the resulting cardiac signals, a biological recorder directly coupled to the electrodes is driven into saturation by the applied pacing pulses. The biological recorder is thus rendered incapable of recording the resulting cardiac signals until recover from saturation. Cardiac signal data occurring during the recovery period is lost.

The ASIC permits more thorough and accurate recovery of cardiac signals in the period immediately following the application of a pacing pulse. To this end, the ASIC can be operated to disconnect the inputs to the biological recorder from the electrodes during the period in which a pacing pulse is applied and to reconnect the electrodes to the biological recorder inputs immediately following application of the pacing pulse. Referring to FIG. 3, the edge detector 64 detects the edges of the applied pacing pulses. The control circuitry 57, by monitoring the occurrence of each applied pacing pulse can, after a small number of pulses have been applied, then determine the pulse duration as well as the pulse application frequency. With such information, the control circuitry 57 can then actuate the ASIC 50 to temporarily disconnect the electrodes 16 from the inputs to the biological recorder 22 during the period in which the pacing pulse is applied and reconnect the electrodes immediately after the applied pacing pulse terminates. By so disconnecting the electrodes 16, the input channels of the biological recorder are never driven into saturation and the biological recorder input channels are immediately ready to record the cardiac signals induced by the applied pacing pulse. Alternatively, the derivative of the pacing pulse can be used to detect the leading and trailing edges of the pacing pulse. Based on this information, the control circuitry 57 can then actuate the ASIC 50 to temporarily disconnect the electrodes 16 when the leading pulse of the pacing pulse occurs and reconnect them immediately after the trailing edge has been detected.

Similarly, adaptive filtering can be used to remove pacing overvoltages and thereby avoid saturation of the biological recorder. Adaptive filtering blocks can be used as functional blocks of the ASIC 50. Suitable adaptive filtering techniques are shown, for example, in the copending application Ser. No. 390,559, filed Feb. 17, 1995, the specification of which is incorporated by reference herein.

It will be appreciated that use of the switching transistor arrangements herein shown and described enable the ASIC to pass the relatively low level cardiac signals sensed by the electrodes 16 while enabling the ASIC to resist without damage the much higher amplitudes of the applied pacing pulses.

Figure 15:
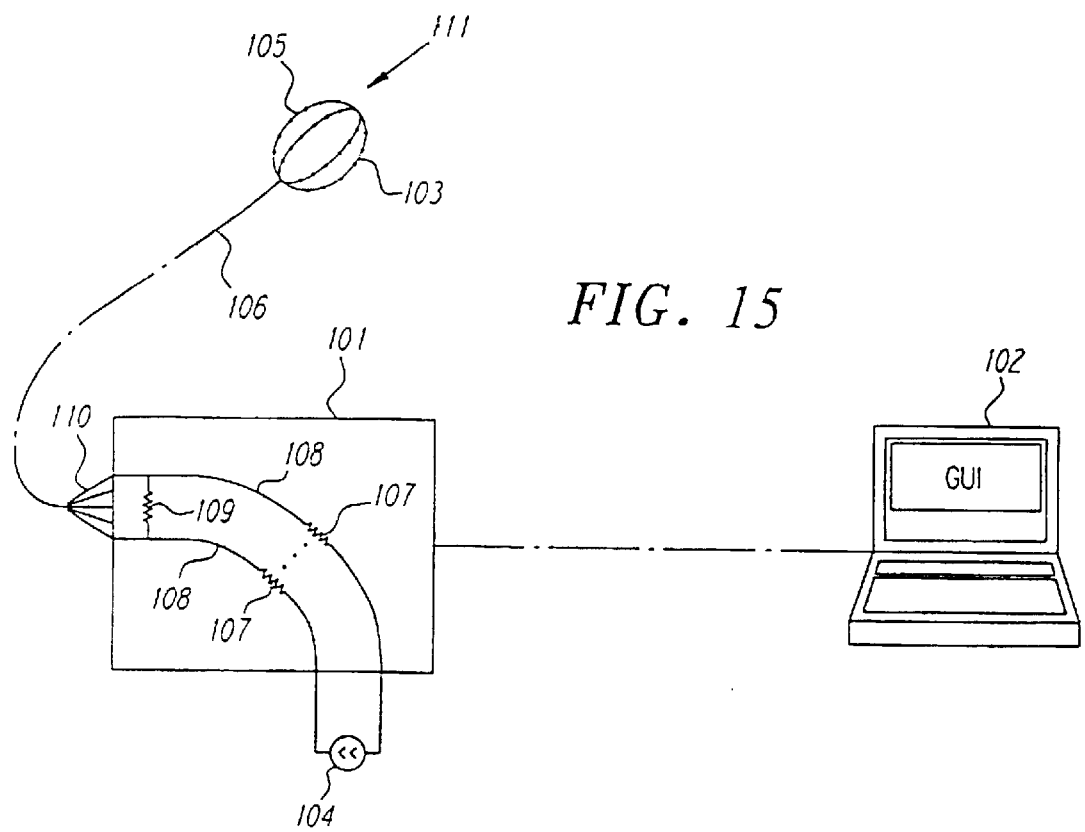
FIG. 15 is a simplified diagram of a cardiac diagnostic and treatment system having a switch driver connectable to a multiple electrode catheter and display interface.

Referring to FIG. 15, in an alternate preferred embodiment, a switch matrix 201 is provided as part of a patient interface system 202 for use in conjunction with multiple electrode catheters, such as basket catheter 211. In particular, the basket catheter 211 includes an elongate catheter body 206 having a plurality of flexible spline elements 203 connected at one end. Each of the spline elements 203 carries a plurality of electrodes 205 adapted for making electrical contact with the internal tissue regions of a patient's heart.

The other end of the catheter body 206 is adapted for connecting to a switch matrix 201. In particular, referring additionally to FIG. 16, a respective electrical lead 210 extends from each electrode 205 through the catheter body 206, with the leads 210 connectable to the switch matrix 201 as respective inputs 222. In this manner, the respective leads 210 provide a separate electrical path from the switch matrix inputs 222 to the respective electrodes 205. The effective path resistance "seen" by each lead 210 through switch elements (not shown) of the switch matrix 201 is represented by a corresponding resistance 207, which may vary for each particular switch path 208 formed through the switch matrix 201. This resistance 207 is preferably minimized, typically between 10–1000Ω in a preferred embodiment.

Each signal path 208 formed through the switch matrix 201 is independent from the other paths, as represented by a high resistance 209 between each path 208. Since the overall resistance seen by an electrode lead 210 at an input 222 of the switch matrix 201 can be relatively large in known patient applications, the switch matrix 201 must operate over a large fluctuating voltage range due to the presence of a varying signal source 204. For example; signal source 204 can be a cardiac stimulator used for pacing or a source of currents used for diagnosis of a patient's heart, or other body organs or functions.

The switch matrix 201 comprises a multiplicity of switch elements, which are preferably implemented by MOSFETs as part of an alternate preferred ASIC. The switch matrix 201 is capable of interconnecting multiple inputs 222 from the catheter 211 to either multiple channel outputs 223 or source receptacles 224. In particular, the switch matrix 201 allows for any input 222 to be selectively connected to any channel 223 or source receptacle 224 output. While FIG. 16 depicts ninety-six inputs 222 selectively connectable to seventy-two channel outputs 223 and/or four cardiac stimulator receptacle outputs 224, it will be appreciated by those skilled in the art that the switch matrix 201 could be modified to provide selective cross-connection of any number of inputs to outputs, including supporting multiple medical diagnosis or therapeutic applications.

Figure 16:
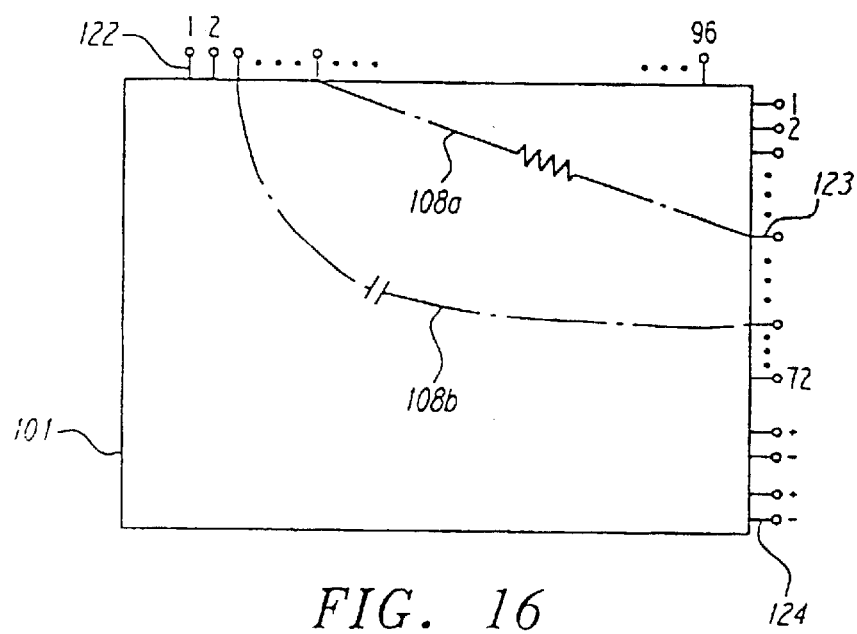
FIG. 16 is a representation of a switch matrix capable of creating electrical paths between multiple electrode inputs and multiple display channel outputs.

In particular, as shown in FIG. 16, when activated into an "ON" condition, a given switch path 208a within the switch matrix 201 behaves as a low value resistor. Switch paths 208b in an OFF condition behave as a high-resistance capacitance, thereby forming an open loop and precluding path formation.

For example, cardiac-pacing currents can vary ±20 mA, as represented by the varying source 204 in FIG. 15. In this instance, source 204 may include a pulsed current source or a low-, medium- or high-frequency voltage or current sources. These currents may include pacing currents, physiological signals, or recording signals. Since the bipolar resistance seen between any two inputs 222 can be up to 1.5 kΩ in human patient applications, a switch path 208 is thereby exposed to a possible voltage swing of over ±30V. However, the reference voltage for a particular switch path will vary with the relative voltage difference of the body potential of a patient. Because this relative voltage can fluctuate, an activated switch matrix path 208a will not always have a fixed reference voltage. Thus, upon activation, transistor substrates (not shown) within the switch matrix 201 must be able to "float" so as to permit the formation of an active switch matrix path 208a, even though the relative voltage may widely fluctuate.

Figure 17:
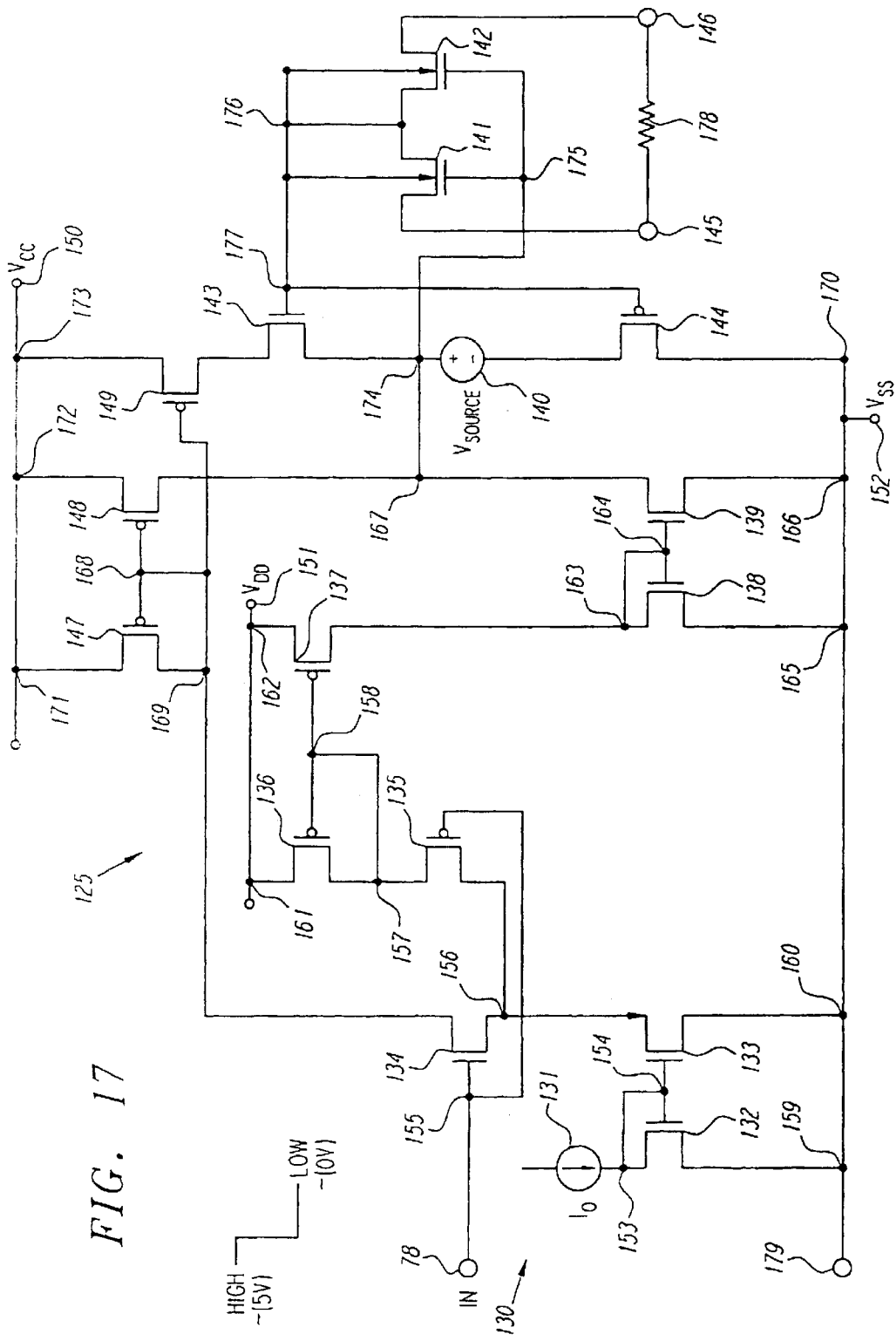
FIG. 17 is schematic diagram of a switch element within the switch matrix of FIG. 16.

Accordingly, referring to FIG. 17, a preferred ASIC 225 is implemented as a CMOS switching circuit which floats with the average body potential of a patient and is capable of withstanding a large voltage variation.

In particular, an input voltage can be applied at 230 between terminals 278 and 279. The positive terminal 278 is connected to the gate of a transistor 234 at node 255. The gate of transistor 234 at node 255 is also connected to the gate of a PMOS transistor 235. The drain of transistor 235 is connected to the source of transistor 234, and the drain of a transistor 233 at node 256. The gate of transistor is tied to a transistor 232 at node 254. The gate of transistor 232 at node 254 is tied to the drain of transistor 232 at node 253. A current source 231 provides a current to the source of transistor 232 at node 253. The source of transistor 232 connects to a relative patient voltage $V_{ss}$ 252 at node 259, while the source of transistor 233 connects to $V_{ss}$ 252 at node 260. $V_{ss}$ 252 is connected to the terminal 279. The current source 231 can be implemented using NMOS transistors. The current can be defined by specifying the width and length of the MOS channel. Typically, the current source 231 generates a few microamps.

The source of transistor 235 connects to the source of a PMOS transistor 236 at node 257. The drain of transistor 236 at node 257 is tied to the gate of transistor 236 at node 258. The source of transistor 236 is tied to voltage source $V_{dd}$ 251 at node 261 and to the source of a transistor PMOS 237 at node 262. The gate of transistor 236 is tied to the gate of transistor 237 to form a current mirror pair. The drain of transistor 237 is tied to the drain of an NMOS transistor 238 at node 263. The gate of transistor 238 is tied to the gate of an NMOS transistor 239 at node 264. The drain of transistor 238 at node 263 is tied to the gate of transistor 238 at node 264 so that transistors 238 and 239 form a basic current mirror pair. The source of transistor 238 is tied to $V_{ss}$ 252 at node 265, and the source of transistor 239 is tied to $V_{ss}$ 252 at node 266.

The drain of transistor 239 is tied to the drain of a PMOS transistor 248 at node 267. The gate of transistor 248 is tied to the gate of a PMOS transistor 247 at node 268. The gate of transistor 247 is tied to the drain of transistor 247 at node 269 so that transistors 247 and 248 form a current mirror. The drain of transistor 247 is tied to the drain of transistor 234 at node 269. Both the source of transistor 248 and the source of transistor 247 are connected to an external source $V_{cc}$ 250 at nodes 272 and 271, respectively. The source of a PMOS transistor 249 is also connected to $V_{cc}$ at node 273. The gate of transistor 249 is tied to the drain of transistor 247 and the drain of transistor 234 at node 269. The drain of transistor 249 is tied to the drain of an NMOS transistor 243.

The source of transistor 243 is tied to a positive terminal of a current-controlled $V_{source}$ 240 at node 274. The positive terminal of $V_{source}$ 240 at node 274 is tied to the drains of transistors 248 and 239 at node 267. The negative terminal of $V_{source}$ 240 is tied to the source of a PMOS transistor 244. The drain of transistor 244 is tied to $V_{ss}$ 252 at node 270. The gate of transistor 243 is tied to the gate of transistor 244 at node 277. The source $V_{source}$ 240 is formed of NMOS transistors and delivers a high/low voltage when the through current is at a high/low value. Its high-voltage value can be defined be specifying the width and length of the MOS channels.

The gates of two NMOS transistors 241 and 242 are tied together at node 275 and connected to $V_{source}$ 240 and the source of transistor 243 at node 274. The drain of a transistor 241 is tied to the source of a transistor 242 at node 276. The gates of transistors 244 and 243, tied together at node 277, are connected to the source of transistor 242 and the drain of transistor 241 at node 276. The source of transistor 241 is connected to a terminal 245 while the drain of transistor 242 connects to a terminal 246. Terminals 245 and 246 connect inputs 222 to outputs 223 or to source receptacles 224, as shown in FIG. 16. The NMOS transistors 241 and 242 form one switch element of the switch matrix 201 in FIG. 15. The ON resistance is defined by specifying the width and length of the MOS channel. The equivalent resistance 278 seen between 245 and 246 can change depending on the current passing between terminals 245 and 246 and depending on the fluctuating voltage build-up between the terminals 245 and 246.

To create the floating substrate characteristic, the ASIC 225 operates with two effective paths: an OFF path and an ON path. The OFF path precludes electrical paths between particular input electrodes and output channels. On the other hand, the ON path configuration triggers the formation of an electrical path 208a between a desired input electrode 222 and a desired channel output 223 or source receptacle 224. In the illustrated preferred embodiment, $V_{cc}$ is typically about +50 V, $V_{dd}$ is −25 V and $V_{ss}$ is −30 V. It will be appreciated by one of skill in the art that the values for $V_{cc}$, $V_{dd}$, and $V_{ss}$ may be modified from these and yet still operatively perform.

The OFF path 208b occurs when the input voltage across terminals 278 and 279 is very close to zero. The ON path 208a has an input voltage that exceeds the threshold voltage and is preferably 5 V.

Figure 20:
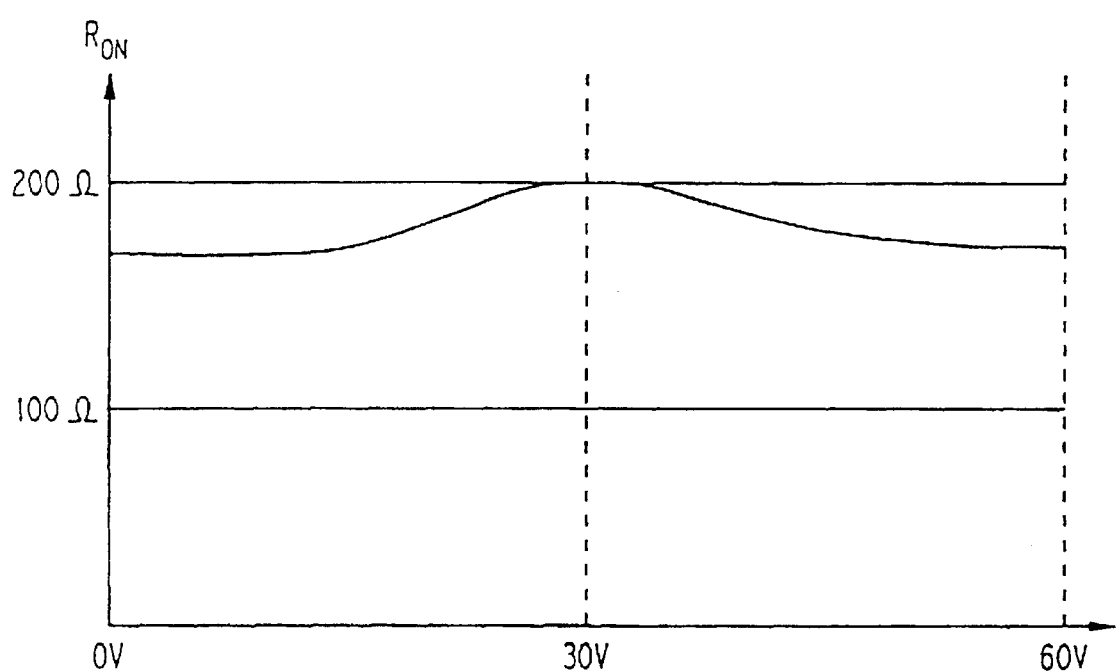
FIG. 20 depicts the impedance/voltage relationship through the effective resistance of the active path configuration shown in FIG. 19.

The resistance seen between terminals 245 and 246 in the OFF configuration is typically greater than 1MΩ. The effective resistance between terminals 245 and 246 in the ON configuration is much less than the 1MΩ seen in the OFF configuration and is preferably between 150 to 200Ω, or lower. FIG. 20 shows a typical dependence of the ON resistance versus the voltage at terminals 245 or 246 with respect to $V_{ss}$. As illustrated, the is ON resistance, $R_{on}$, varies slightly with voltage within the operating range.

For a better understanding of the ASIC 225, we will look first at OFF operation and then at ON operation.

Referring to FIG. 17, in the OFF configuration the voltage across the input 230 between terminals 278 and 279 is approximately 0 V. In this configuration no switch matrix path is established. For both the OFF and ON configurations, $I_0$ from the current source 231 preferably is 2 μA. The current from current source 231 passes through a first basic current mirror consisting of two matched NMOS transistors 232 and 233. Due to the characteristics of a current mirror, the output current at the drain of transistor 233 remains close to 2 μA. Since $V_{in}$ between terminals 278 and 279 is 0 V, the output current from this first current mirror passes away from the NMOS transistor 234 through the drain of the PMOS transistor 235.

The current at the source of the PMOS transistor 235 is passed to a second current mirror pair consisting of matched PMOS transistors 236 and 237. Again, due to the characteristic of a current mirror, the current $I_0$ at the source of PMOS transistor 236 is about equal to the current at the source of transistor 237 toward the third current mirror comprising NMOS transistors 238 and 239. Since transistor 239 conducts, it forces the current to flow away from $V_{source}$ 240. Therefore, the voltage seen across $V_{source}$ 240 is 0 V in an OFF configuration. Current from $V_{cc}$ 150 will pass through transistor 149, transistor 243 and through transistor 239 to $V_{ss}$, bypassing $V_{source}$. Because $V_{source} \approx 0$ V, the gate-to-source voltages of transistors 241 and 242 are close to 0 V. Therefore, transistors 241 and 242 do not conduct and the switch element is OFF.

For the OFF configuration, a path between a particular input 222 and channel output 223 or source receptacle 224 will not be activated and is therefore not connected in switch matrix 201 despite the presence of a floating reference voltage. In the ON configuration, preferably 5 V are applied at the input 230 across terminals 278 and 279. This voltage difference is selected to be high enough to switch NMOS transistors on but not so high as to make the switching circuit impracticable.

For the ON configuration, $I_0 \approx 2$ μA from current source 231 passes through a first basic current mirror consisting of the two matched NMOS transistors 232 and 233. Due to the characteristics of the current mirror, the output current at the drain of transistor 233 is similarly $I_0 \approx 2$ μA. The 2 μA is then seen at the source of transistor 234. The current at the drain of transistor 234 passes to the current mirror comprising matched PMOS transistors 247 and 248. Because of the characteristic of the current mirror to maintain current linearity, the current level maintained at the drain of transistor 248 is directed to $V_{source}$ 240. Thus, in the ON configuration current from transistors 248 and 249 flows to the current-controlled $V_{source}$ 240 since transistor 239 will be effectively off. Transistor 243 will also be off because it will have a negative gate-to-source voltage.

The $V_{source}$ 240 is selected to be sufficiently high to overcome the threshold of the NMOS circuitry 241 and 242. The voltage level at the output of $V_{source}$ 240 at node 274 must also overcome the feedback gate-to-source voltage of PMOS transistor 244. Since this gate-to-source voltage of transistor 244 is approximately 2–3 V, $V_{source}$ 240 in the preferred embodiment is about 22 V, and the voltage appearing gate-to-source at transistors 241 and 242 comes out to be about 19 to 20 V. It will be appreciated by one skilled in the art that $V_{source}$ 240 can take on other values but primarily so long as sufficiently high to properly bias the circuitry and overcome the feedback voltage.

Figure 18:
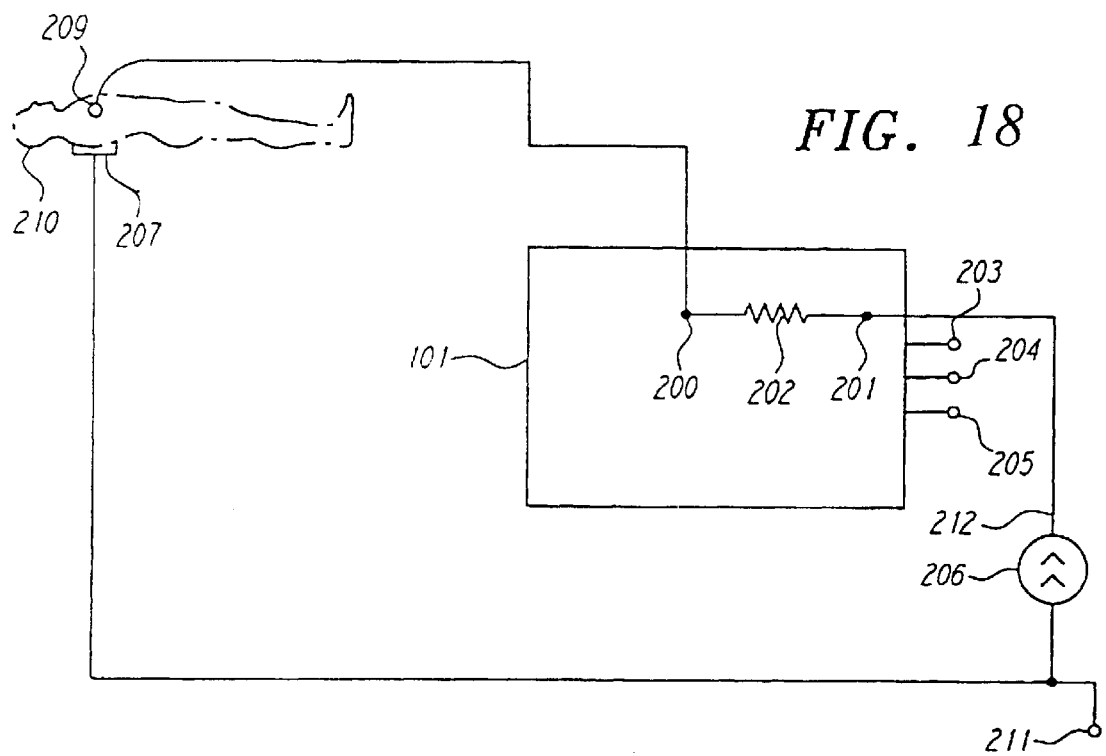
FIG. 18 is a simplified representation of a switch matrix forming an electrical path configuration through a patient.

FIG. 18 diagrammatically represents operation of the switch matrix 201 supporting an active electrical path 312 through a patient 310, in conjunction with an exemplary pacing application. In particular, the switch matrix 201 is connected to a current source 306 at terminal 246, with the current source 306 is connected to a patient ground 311. The current source 306 represents the current created by a pacemaker (not shown). The switch matrix 201 has $V_{cc}$, $V_{dd}$, and $V_{ss}$ connected at outputs 303, 304 and 305, respectively. Terminals 245 and 246 of the ASIC 225 are represented by nodes 300 and 301 having a resistance 302 between them. In particular, resistance 302 represents the resistance from transistors 241 and 242 when in the ON configuration. Terminal 200 is shown connected to the heart of a patient 310. In a preferred embodiment, resistance 302 is relatively low, e.g., approximately 300Ω. The electrical path 312 also includes a pacing electrode 309 disposed in the patient 310. A reference electrode 307 electrically couples the patient 310 to patient ground 311.

During operation, i.e., when the portion of the electrical path 312 through the switch matrix 201 is "ON, the patient/ pacing impedance is that impedance seen by the path 312 from node 300 to electrode 307, via the patient 310. This impedance primarily includes the myocardial tissue impedance of the patient 310. In known applications, this impedance can be up to 1.5 kΩ. Thus, the voltage that develops at 300 or 301 with respect to patient ground 311 is approximately equal to the current from the pacing source 306 times the patient/pacing impedance (represented by resistance 320 in FIG. 19). As indicated above, this current typically varies ±20 mA. Thus, under "worst case" conditions, the voltage that develops on terminals 245 and 246 of the ASIC 225 with respect to patient ground 311 can reach approximately ±30 V. However, the voltage difference that simply develops between terminals 245 and 246 is only ±20 mA times the resistance 321. Under similar worst case conditions, this voltage difference between terminals 245 and 246 can reach approximately ±4 V.

Thus, in the ON configuration the NMOS substrate compensates or floats so as to permit the formation of a switch matrix path 208a even though the relative patient voltage may fluctuate as much as ±30V. Therefore, in an ON configuration, a switch matrix path can be established despite substantial fluctuations in reference voltage and current caused by a pacemaker or current source 204. However, even in an OFF configuration, it is possible that terminals 245 and 246 can still be exposed to voltage extremes of about ±30 V. This voltage extreme can occur in the switch matrix 201 where some paths are off while adjacent or neighboring paths are on. Thus, where one terminal such as 246 is connected to a patient, terminal 245 for one switch path 208a will be ON while a terminal 245 for another switch path 208b may be OFF. In such a situation, the voltage can build up between a terminal 245 and 246 for an unactivated path 208b and reach about ±30 V. Therefore, the ASIC 225 may be exposed to a voltage range of ±30 V in either an OFF or ON configuration.

While preferred embodiments of the invention have been shown and described, it will be obvious to those skilled in the art that changes and modifications can be made without departing from the invention in its broader aspects, and, therefore, the aim in the appended claims is to cover all such changes and modifications as fall within the true spirit and scope of the invention.

We claim:
1. A system for transmitting or receiving signals to or from a non-fixed physiological load or source, comprising:
a switch having an input, an output and a switch path, the input and output being selectively couplable though the switch path, wherein the switch path is configured to float with respect to the non-fixed load or source.
2. The system of claim 1, wherein the non-fixed physiological load or source is a patient's relative myocardial potential.
3. The system of claim 1, wherein the switch path is configured to withstand relative current fluctuations.
4. The system of claim 3, wherein the relative current fluctuations are caused by physiological events occurring in the non-fixed physiological load or source.
5. The system of claim 1, wherein the switch path is bi-directional.
6. The system of claim 1, wherein the switch includes an interface operable to receive generated commands.
7. The system of claim 1, wherein the input is adapted to receive physiological signals from a multiple electrode catheter.
8. The system of claim 1, wherein the output is couplable to a display device.
9. The system of claim 1, wherein the output is couplable to a biological recorder.
10. The system of claim 1, further comprising test circuitry for detecting the existence of abnormal operating conditions.
11. The system of claim 1, wherein the switch path includes circuitry configured to withstand a relative voltage difference of at least ±30V.
12. The system of claim 1, wherein the switch path includes circuitry configured to withstand a relative voltage difference up to a maximum relative voltage swing of the physiological load or source.
13. The system of claim 1, wherein the switch path includes circuitry having a floating substrate.
14. The system of claim 1, wherein the switch path includes circuitry comprising means for establishing a first path where current flows away from a voltage source when an input voltage is below a threshold level, means for establishing a second path where current flows to the voltage source when the input voltage exceeds the threshold level, and feedback circuitry configured to maintain a feedback voltage when the second path is established.
15. A system for monitoring physiological signals from a non-fixed physiological source, comprising:
a switch matrix having a plurality of inputs, a plurality of outputs, and a plurality of switch paths, the plurality of inputs each being adapted to receive physiological signals, the plurality of outputs each being couplable to external devices for displaying or processing the physiological signals, the plurality of inputs each being selectively connectable to one of the plurality of outputs through the plurality of switch paths, wherein the plurality of switch paths are configured to float with respect to the non-fixed load or source.

16. The system of claim 15, wherein the plurality of switch paths include circuitry configured to float with respect to the non-fixed physiological source.

17. The system of claim 15, wherein the plurality of switch paths include circuitry configured to withstand a relative voltage difference up to a maximum relative voltage swing of the non-fixed physiological source.

18. The system of claim 15, further comprising a control circuit, the control circuit being configured to activate at least one of the plurality of switch paths in accordance with applied commands.

19. The system of claim 15, wherein the non-fixed physiological source is a patient's relative myocardial potential.

20. The system of claim 15, wherein the plurality of switch paths include circuitry having a floating substrate.

21. A system operable to selectively couple non-fixed physiological signals with at least one output channel, comprising:

a switch having a input channel, an output channel and a switch path, the input channel being selectively couplable to the output channel through the switch path, wherein the switch path includes an electrical circuit configured to float with respect to a non-fixed physiological load or source.

* * * * *

UNITED STATES PATENT AND TRADEMARK OFFICE
CERTIFICATE OF CORRECTION

PATENT NO. : 6,615,073 B1
DATED : September 2, 2003
INVENTOR(S) : Dorin Panescu et al.

Figure 19:
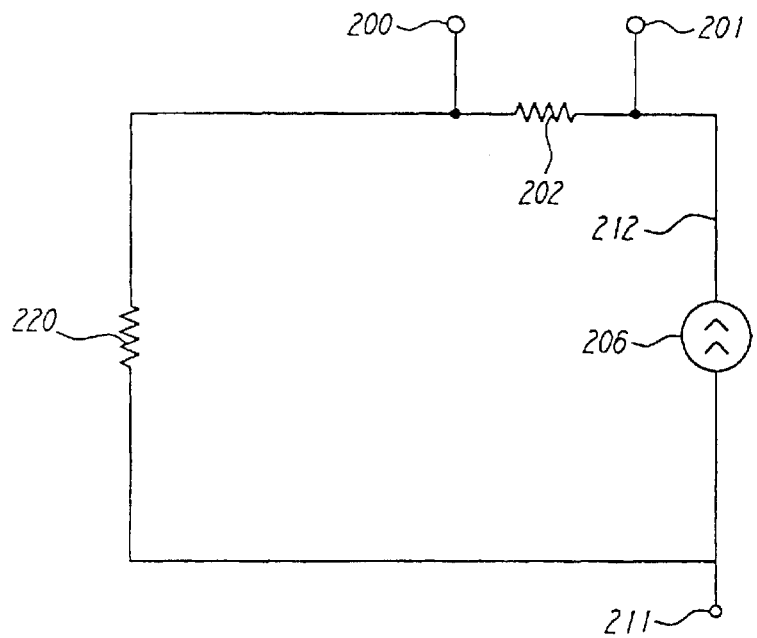
FIG. 19 is a general circuit equivalent for an active path configuration of the switch matrix of FIG. 18.

It is certified that error appears in the above-identified patent and that said Letters Patent is hereby corrected as shown below:

Drawings,
FIG. 15, please delete the follow labeling numbers: "101", "102", "103", "104", "105", "106", "107", "108", "109", "110", and "111", and replace them with corresponding numbers: -- 201 --, -- 202 --, -- 203 --, -- 204 --, -- 205 --, -- 206 --, -- 207 --, -- 208 --, -- 209 --, -- 210 --, and -- 211 --.
FIG. 16, please delete labeling numbers: "101", "108a", "108b", "122", "123", and "124" and replace them with corresponding numbers: -- 208a --, -- 208b --, -- 201 --, -- 222 --, -- 223 --, and -- 224 --.
FIG. 17, please delete labeling numbers: "78", "125", "130", "131", "132", "133", "134", "135", "136" "137" "138", "139" "140", "141", "142" "143" "144" "145", "146" "147" "148" "149" "150" "151" "152" "153" "154" "155" "156" "157", "158" "159" "160" "161" "162" "163" "164" "165","166" "167" "168" "169", "170", "171", "172" and replace them with corresponding numbers: -- 178 --, -- 225 --, -- 230 --, -- 231 --, -- 232 --, -- 233 --, -- 234 --, -- 235 --, -- 236 --, -- 237 --, -- 238 --, -- 239 --, -- 240 --, -- 241 --, -- 242 --, -- 243 --, -- 244 --, -- 245 --, -- 246 --, -- 247 --, -- 248 --, -- 249 --, -- 250 --, -- 251 --, -- 252 --, -- 253 --, -- 254 --, -- 255 --, -- 256 --, -- 257 --, -- 258 --, -- 259 --, -- 260 --, -- 261 --, -- 262 --, -- 263 --, -- 264 --, -- 265 --, -- 266 --, -- 267 --, -- 268 --, -- 269 --, -- 270 --, -- 271 --, -- 272 --.
FIG. 18, please delete labeling numbers: "101", "200", "201", "202", "203", "204", "205", "206", "207", "209", "210", "211", "212" and replace them with corresponding numbers: -- 201 --, -- 300 --, -- 301 --, -- 302 --, -- 303 --, -- 304 --, -- 305 --, -- 306 --, -- 307 --, -- 309 --, -- 310 --, -- 311 --, -- 312 --.
FIG. 19, please delete labeling numbers: "200", "201", "202", "206", "220", "211", "212" and replace them with corresponding numbers: -- 300 --, -- 301 --, -- 302 --, -- 306 --, -- 320 --, -- 311 --, -- 312 --

Signed and Sealed this

First Day of March, 2005

JON W. DUDAS
*Director of the United States Patent and Trademark Office*